United States Patent
Xiao et al.

(10) Patent No.: US 9,133,203 B2
(45) Date of Patent: Sep. 15, 2015

(54) PYRROLOQUINAZOLINE COMPOUNDS

(71) Applicants: Xiangshu Xiao, Portland, OR (US);
Jingjin Chen, Portland, OR (US);
Bingbing Li, Portland, OR (US)

(72) Inventors: Xiangshu Xiao, Portland, OR (US);
Jingjin Chen, Portland, OR (US);
Bingbing Li, Portland, OR (US)

(73) Assignee: OREGON HEALTH & SCIENCE UNIVERSITY, Portland, OR (US)

( * ) Notice: Subject to any disclaimer, the term of this patent is extended or adjusted under 35 U.S.C. 154(b) by 0 days.

(21) Appl. No.: 14/309,715

(22) Filed: Jun. 19, 2014

(65) Prior Publication Data

US 2014/0378486 A1  Dec. 25, 2014

Related U.S. Application Data

(60) Provisional application No. 61/837,568, filed on Jun. 20, 2013.

(51) Int. Cl.
*C07D 487/04* (2006.01)

(52) U.S. Cl.
CPC .................................. *C07D 487/04* (2013.01)

(58) Field of Classification Search
CPC ..................................................... C07D 487/04
See application file for complete search history.

(56) References Cited

FOREIGN PATENT DOCUMENTS

JP          2003342276    *    3/2003    ............. A01N 43/90

* cited by examiner

*Primary Examiner* — Erich A Leeser
(74) *Attorney, Agent, or Firm* — Jeffrey M. Jackson

(57) ABSTRACT

Disclosed herein are acylated derivatives of 7H-pyrrolo[3,2-f]quinazoline-1,3-diamine and pharmaceutical compositions comprising said derivatives.

9 Claims, 4 Drawing Sheets

PYRROLOQUINAZOLINE COMPOUNDS

ACKNOWLEDGEMENT OF GOVERNMENT SUPPORT

This invention was made with support of the United States government under the terms of Grant Number RO1GM087305, awarded by the National Institutes of Health. The United States government has rights to this invention.

FIELD

Generally, the disclosure relates to compounds that may be used in pharmaceutical compositions. More specifically, the disclosure relates to 7H-pyrrolo[3,2-f]quinazoline-1,3-diamine derivatives.

BACKGROUND

7H-Pyrrolo[3,2-f]quinazoline-1,3-diamine (Compound 1 herein) and its derivatives, originally synthesized as antifolates in the 1970s (U.S. Pat. No. 4,118,561, (1978); incorporated by reference herein) have been shown to possess a variety of biological activities including antibacterial, anticancer and antiparasitic activity (Gamo F J et al, *Nature* 465, 305-310 (2010); Kuyper L F et al, *J Med Chem* 39, 892-903 (1996); Li Q et al, *Antimicrob Agents Chemother* 51, 2898-2904 (2007); all of which are incorporated by reference herein). Antiviral activity against herpes simplex virus (HSV) has also been reported (Dicker I B et al, *Antiviral Res* 28, 213-224 (1995); incorporated by reference herein).

The biochemical targets for these compounds include dihydrofolate reductase (DHFR) from various species, thrombin receptors, and protein tyrosine phosphatase 1B (PTP1B) McCormack J J et al, *Biochem Pharmacol* 28, 3227-3229 (1979); Ahn H S et al, *Bioorg Med Chem Lett* 9, 2073-2078 (1999) Nadal-Wollbold F, *Eur J Pharmacol* 644, 188-194 (2010); WO 2004101568 (2004); Cheung A W et al, *Bioorg Med Chem Lett* 22, 7518-7522 (2012); all of which are incorporated by reference herein.) The wide spectrum bioactivity of Compound 1 is specific because a survey of the target-based and phenotypic screening assays involving Compound 1 in PubChem (http://pubchem.ncbi.nlm.nih.gov/) show it is only active in 35/528 or 6.6% of the assays suggesting that this particular chemotype is a privileged scaffold that is intrinsically useful for different biological targets (Evans B E et al, *J Med Chem* 31, 2235-2246 (1988) and Welsch S A et al, *Curr Opin Chem Biol* 14, 347-361 (2010), both of which are incorporated by reference herein).

SUMMARY

Disclosed herein are compounds of formula (I)

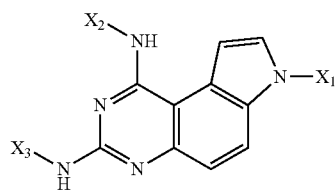

wherein $X_1$, $X_2$, and $X_3$ are independently H or acyl provided that $X_1$, $X_2$, and $X_3$ are not all H. Examples include the compounds of formula (II)

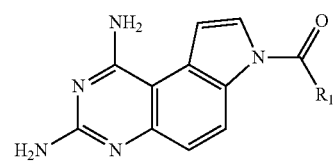

wherein $R_1$ may be any of lower alkyl, ether, or aryl. In still further examples of the compounds, $R_1$ may be methyl, ethyl, propyl, isopropyl, silyl ether, or benzyl, substituted benzyl, naphthyl or substituted naphthyl. Further examples include the compounds of formula (III)

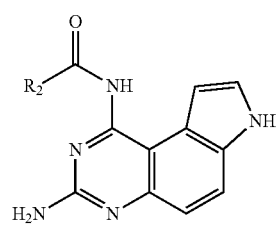

wherein $R_2$ may be any of lower alkyl, ether, or aryl. In still further examples of the compounds, $R_2$ may be methyl, ethyl, propyl, isopropyl, silyl ether, benzyl, substituted benzyl, naphthyl, or substituted naphthyl. Further examples include the compounds of formula (IV)

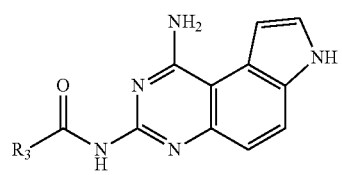

wherein $R_3$ may be any of lower alkyl, ether, or aryl. In still further examples of the compounds, $R_3$ may be methyl, ethyl, propyl, isopropyl, silyl ether, benzyl, substituted benzyl, or naphthyl or substituted naphthyl. Additionally disclosed are pharmaceutical compositions comprising the disclosed compounds.

It is an object of the invention to provide compounds with surprisingly improved potency over 7H-Pyrrolo[3,2-f]quinazoline-1,3-diamine.

It is an object of the invention to provide compounds with different molecular targets than 7H-Pyrrolo[3,2-f]quinazoline-1,3-diamine.

DETAILED DESCRIPTION

Figure 1:
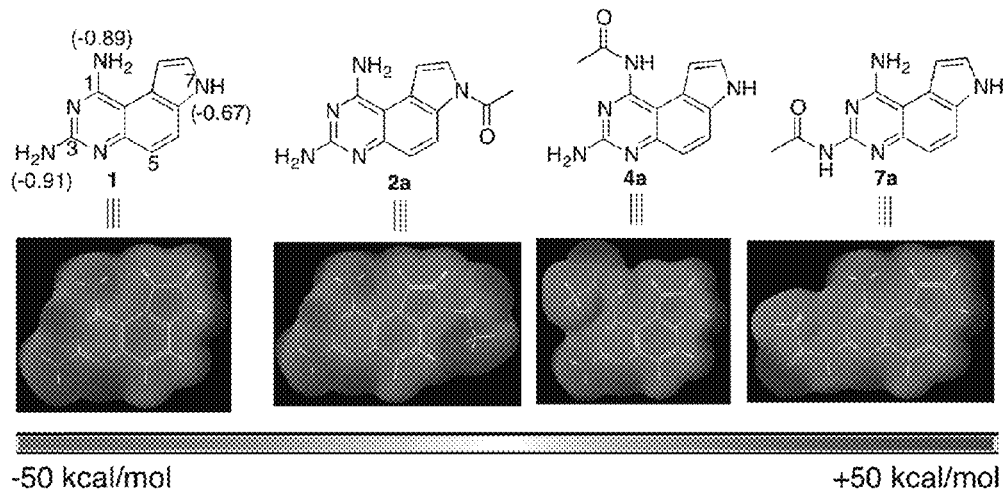
FIG. 1 depicts the chemical structures of compounds 1, 2a, 4a, and 7a (top) and their corresponding molecular electrostatic potential (MEP) surfaces (bottom). MEP surfaces were calculated at an HF/6-31G level of theory and mapped onto their electron densities. The Mulliken atomic charges, also calculated at HF/6-31G level of theory on N1, N3, and N7 of compound 1 are indicated in the parentheses. All the surfaces were normalized from −50 kcal/mol to +50 kcal/mol.

Disclosed herein are compounds of formula (I)

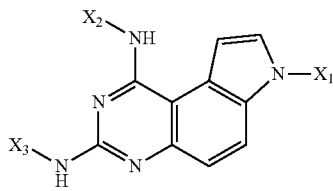

wherein $X_1$, $X_2$, and $X_3$ are independently H or acyl provided that $X_1$, $X_2$, and $X_3$ are not all H.

The following explanations of terms and methods are provided to better describe the present compounds and compositions, and to guide those of ordinary skill in the art in the practice of the present disclosure. It is also to be understood that the terminology used in the disclosure is for the purpose of describing particular embodiments and examples only and is not intended to be limiting. As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. Variables such as $X_1$, $X_2$, $X_3$, $R_1$, $R_2$, and $R_3$, used throughout the disclosure are the same variables as previously defined unless stated to the contrary.

"Administration of" and "administering a" compound refers to providing a compound or a pharmaceutical composition comprising a compound as described herein. The compound or composition can be administered by another person to the subject or it can be self-administered by the subject.

The term "acyl" refers to a C=O group which is attached to two other moieties through the carbon atom. As used herein, it is attached to one of the moieties via a covalent bond with a nitrogen atom. The other groups may be alkyl, lower alkyl, alkenyl, alkynyl, ether, silyl ester, aryl, heterocylic, heteroaliphatic, heteroaryl, and the like. The acyl group may be substituted by any other substitutent including halo, cyano, nitro, oxo, thioxo, trimethylsilanyl, t-butylsilyl ether, or any other.

The term "alkyl" refers to a branched or unbranched saturated hydrocarbon group, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. Alkyl groups may be "substituted alkyls" wherein one or more hydrogen atoms are substituted with a substituent such as halogen, cycloalkyl, alkoxy, amino, hydroxyl, aryl, or carboxyl.

The term "aryl" refers to any carbon-based aromatic group including, but not limited to, benzyl, naphthyl, phenyl, and oxazole. The term "aryl" also includes heteroaryl, which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ether, ketone, aldehyde, hydroxy, carboxylic acid, cyano, amido, haloalkyl, haloalkoxy, or alkoxy, or the aryl group can be unsubstituted.

"Derivative" refers to a compound or portion of a compound that is derived from or is theoretically derivable from a parent compound.

The terms "pharmaceutically acceptable salt" or "pharmacologically acceptable salt" refers to salts prepared by conventional methods that include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methylglutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

These salts may be prepared by standard procedures, for example by reacting the free acid with a suitable organic or inorganic base. Any chemical compound recited in this specification may alternatively be administered as a pharmaceutically acceptable salt thereof. Pharmaceutically acceptable salts are also inclusive of the free acid, base, and zwitterionic forms. Descriptions of suitable pharmaceutically acceptable salts can be found in Handbook of Pharmaceutical Salts, Properties, Selection and Use, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66, 1 (1977).

The term "ether" refers to a group with an R—O—R structure wherein R represents any chemical moiety. Silyl ethers have a $(R)_3$—Si—O—R structure wherein R represents any chemical moiety. Examples of silyl ethers include tert-butyldimethylsilyl ether, tert-butyldiphenyl silyl ether, diphenylmethyl silyl ether, and tri(isopropyl)silyl ether.

Protected derivatives of the disclosed compounds also are contemplated. A variety of suitable protecting groups for use with the disclosed compounds are disclosed in Greene and Wuts Protective Groups in Organic Synthesis; 5 3rd Ed.; John Wiley & Sons, New York, 1999. In general, protecting groups are removed under conditions which will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxyl functions amino is trityl. Other conventional protecting groups are known and suitable protecting groups can be selected by those of skill in the art in consultation with Greene and Wuts Protective Groups in Organic Synthesis; 3rd Ed.; John Wiley & Sons, New York, 1999.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

The compounds disclosed herein may be included in pharmaceutical compositions (including therapeutic and prophylactic formulations), typically combined together with one or more pharmaceutically acceptable vehicles or carriers and, optionally, other therapeutic ingredients.

Such pharmaceutical compositions can formulated for administration to subjects by a variety of mucosal administration modes, including by oral, rectal, intranasal, intrapulmonary, intravitrial, or transdermal delivery, or by topical delivery to other surfaces including the eye. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other examples, the compound can be administered ex vivo by direct exposure to cells, tissues or organs originating from a subject.

To formulate the pharmaceutical compositions, the compound can be combined with various pharmaceutically acceptable additives, as well as a base or carrier useful in the dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween®80), solubility enhancing agents (for example, cyclodextrins and derivatives thereof), stabilizers (for example, serum albumin), and reducing agents (for example, glutathione) can be included.

When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7. The compound can be dispersed in a carrier, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof.

Alternatively or additionally, synthetic fatty acid esters such as polyglycerin fatty acid esters, sucrose fatty acid esters and the like can be employed as carriers. Hydrophilic polymers and other vehicles can be used alone or in combination, and enhanced structural integrity can be imparted to the vehicle by partial crystallization, ionic bonding, cross-linking and the like. The carrier can be provided in a variety of forms, including fluid or viscous solutions, gels, pastes, powders, microspheres, and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanoparticles prepared from a suitable polymer, for example, 5 isobutyl 2-cyanoacrylate (see, for example, Michael et al., *J. Pharmacy Pharmacol.* 43, 1-5, 1991), and dispersed in a biocompatible dispersing medium, which yields sustained delivery and biological activity over a protracted time. Alternatively, the compound may be combined with a mesoporous silica nanoparticle including a mesoporous silica nanoparticle complex with one or more polymers conjugated to its outer surface.

The pharmaceutical compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional non-toxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like. Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DL-lactic acidco-glycolic acid), poly(D-lactic acid-co-glycolic acid), and poly(L-lactic acid-coglycolic acid). Other useful biodegradable or bioerodible polymers include, but are not limited to, such polymers as poly(epsilon-caprolactone), poly(epsilon-aprolactone-CO-lactic acid), poly(epsilon.-aprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, Sustained and Controlled Release Drug Delivery Systems, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

EXAMPLES

The following examples are illustrative of disclosed methods. In light of this disclosure, those of skill in the art will recognize that variations of these examples and other examples of the disclosed method would be possible without undue experimentation.

Example 1

Selective $N^7$-Acylation of Compound 1

Acylation preceded by the following reaction:

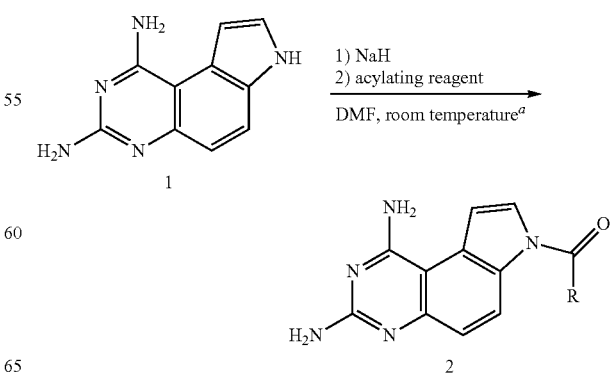

TABLE 1

$N^7$ acylation of compound 1.

| Acylating reagent structure | Acylating reagent ID | R Group | Product ID | % Yield |
|---|---|---|---|---|
| $(CH_3CO)_2O$ | 3a | Methyl | 2a | 78 |
| $(CH_3CH_2CO)_2O$ | 3b | Ethyl | 2b | 78 |
| $(CH_3CH_2CH_2CO)_2O$ | 3c | Propyl | 2c | 73 |
| $[(CH_3)_2CHCO]_2O$ | 3d | Isopropyl | 2d | 78 |
| $TBSO(CH2)_4COOSu$ | 3e | $TBSO(CH_2)_4$ | 2e | 68 |
| 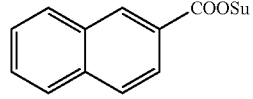 | 3f | 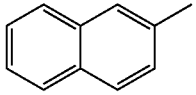 | 2f | 91 |

Compound 1 was treated with NaH (1.1 equivalents) in DMF for 1 hour. Then an acylating reagent (1.1 equivalents was added.) The yields refer to isolated yields.

It is predicted that the proton attached to $N^7$ is most acidic, however, the pKas of the protons attached to $N^1$ and $N^3$ are probably comparable. To further investigate this point, the structure of compound 1 was optimized at HF/6-31G** level of theory and the Mulliken atomic charges (Mulliken R S, *J Chem Phys* 23, 1833-1840 (1955); incorporated by reference herein) were calculated (Xiao X et al, *J Med Chem* 48, 3231-3238 (2005); incorporated by reference herein.) Consistent with the prediction, $N^7$ is the least negatively charged among the three ionizable nitrogen atoms (FIG. 1). $N^1$ is slightly less charged than $N^3$, suggesting that the order of pKa is $N^7 < N^1 \leq N^3$. Therefore, it was speculated that $N^7$—H could be selectively deprotonated and acylated.

Compound 1 was prepared from 5-aminoindole using a reported procedure with slight modifications in 82% yield (Jones M L et al, *J Heterocycl Chem* 31, 1681-1683 (1994); incorporated by reference herein). The synthesized compound 1 was deprotonated by NaH followed by treatment with acetic anhydride (3a), resulting in compound 2a obtained in 78% yield (Table 1). The diagnostic loss of $N^7$—H at 11.55 ppm and loss of a triplet at 7.43 ppm attributed to $C^8$—H in compound 1 supported the hypothesis that the acetyl group was attached to $N^7$. A few other anhydrides (3b, 3c, and 3d in Table 1) were used as acylating reagents and the corresponding $N^7$-acylated products were obtained in comparable yields (Table 1).

Due to the limited commercial availability of anhydrides and the loss of an acyl equivalent during reactions using anhydrides, the utility of N-hydroxysuccinimide (NHS) esters as the acylating regents was investigated. Both aliphatic and aromatic carboxylic NHS esters were found to react smoothly to give the $N^7$ acylated compounds in good to excellent yields (entries 5-6, Table 1). The TBS group in 3e was well tolerated.

The discovery of NHS esters as efficient acylating agents substantially expands the variety of $N^7$ acylated compounds that can be prepared through this route. In general, the $N^7$ acylated compounds of Series 2 are sparingly soluble in common organic solvents or water. Therefore, most of the products were not purified by column chromatography, but they were all found to be >95% pure based on $^1$H NMR analyses. In the case of 2a, 2b, and 2c, the solubility was so limited that high-quality $^{13}$C NMR spectra could not be obtained.

Example 2

Synthesis of $N^1$-Acylated Compounds of Series 4

Acylation of compounds of Series 4 was performed by the following reaction:

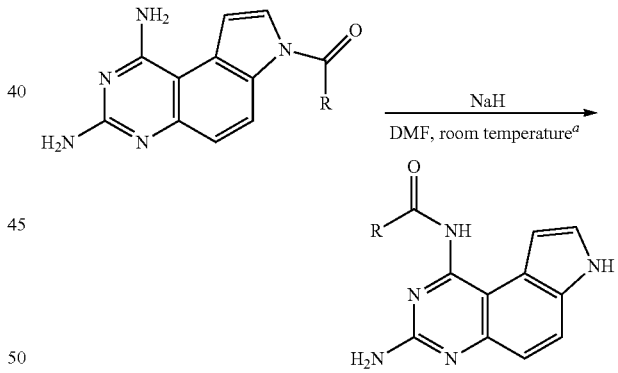

These yielded the compounds of Series 4:

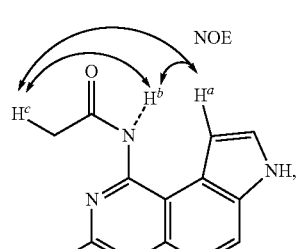

4a

24%

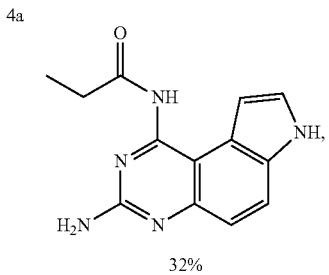

4b

32%

-continued

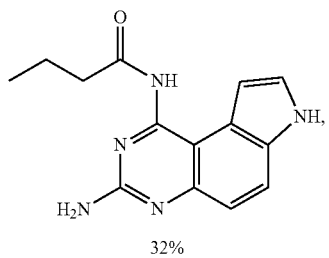
4c
32%

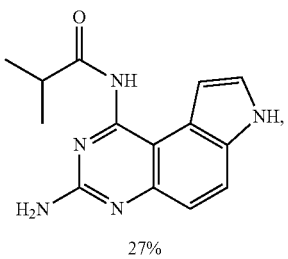
4d
27%

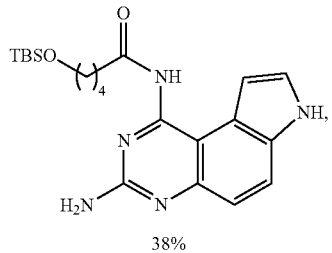
38%

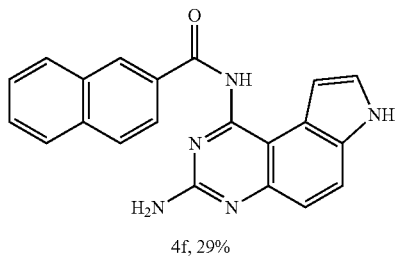
4f, 29%

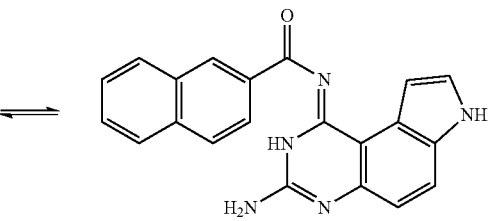
4f'

[a] The reactions were carried out with compounds 2 from Table 1 (1.0 equivalents) and NaH (1.1 equivalents) in DMF. The yields refer to isolated yields.

4f and 4f' are a 1:1 mixture of two tautomers in DMSO-$d_6$.

$N^1$ and $N^3$ were predicted to be more nucleophilic than $N^7$, however, all attempts to direct acetylation of either $N^1$ or $N^3$ in compound 1 with $Ac_2O$ failed to provide selectively mono-N-acetylated products. After considerable experimentation, it was found that treatment of 2a with NaH resulted in $N^1$-acetylated product 4a in 24% yield. The regioselectivity of this reaction was confirmed by the positive nuclear Overhauser effect (NOE) between Ha and Hb, Ha and Hc observed in 4a. Without being bound by theory, the mechanism for this transformation presumably involves an intermolecular acetyl transfer from $N^7$ of one molecule to $N^1$ of the other molecule followed by cleavage of $N^7$-acetyl group from the latter molecule. The major byproduct generated from this reaction was the deacetylated compound 1, which was isolated in 74% yield.

The combined yields of 1 and 4a accounted for nearly quantitative recovery of 2a. The absence of $N^3$-acylated product from this reaction supported the prediction of $pK_a$ order of $N^1 < N^3$ (FIG. 1) and illustrated that subtle differences in $pK_a$ can be synthetically exploited. All the aliphatic acylated substrates 2a-2e were successfully converted into $N^1$-acylated products 4a-4e in 24-38% isolated yields (Table 2). In the case of aromatic acylated compound 4f, it was obtained in 29% yield existing as a 1:1 mixture of two clearly NMR-distinguishable tautomers 4f and 4f' in DMSO-$d_6$. This tautomeric mixture becomes a single tautomer 4f upon treatment with an aqueous NaOH solution. In addition, all the active protons in 4f disappeared in its $^1H$ NMR due to H-D exchange with HDO generated from the reaction of NaOH with DMSO-$d_6$. For the same reason, the signals from the residual solvents in both $^1H$ NMR and $^{13}C$ NMR spectra were very complicated.

It was also found that different bases exerted a great effect on the yield of this acyl transfer reaction. For example, LDA resulted in a 0% yield of 4a while a 45% yield of 4a was obtained if LiHMDS was used as a base (see Table 2). Similarly, a 50% yield of 4f and 4f' resulted when LiHMDS was used as the base.

Table 2 The effect of different bases on the yield of compound 4a from compound 2a.

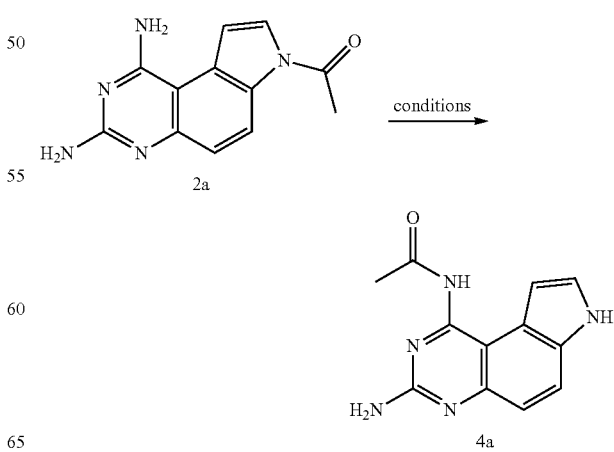

TABLE 2 effect of bases on yields of compounds of series 4

| Base | Temp (° C.) | Yield (%)[a] |
|---|---|---|
| NaH | 25 | 24 |
| LDA | 25 | 0 |
| NaO$^t$Bu | 25 | 25 |
| LiHMDS | 25 | 35[b] |
| LiHMDS | 0 | 45 |
| LiHMDS | −20 | 40 |

[a]Isolated yields
[b]Containing about 10% of 4a' as assessed by $^1$H NMR.
Structure of compound 4a'

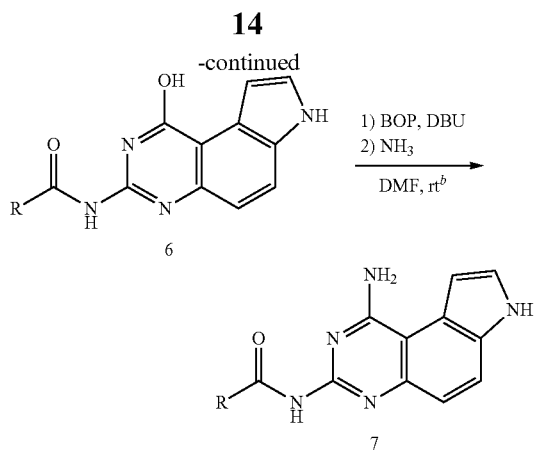

TABLE 3

N$^3$ acetylated compounds:

| Acylating reagent structure | Acylating reagent ID | R Group | Yield 6 | 6 | Yield 7 | 7 |
|---|---|---|---|---|---|---|
| (CH$_3$CO)$_2$O | 3a | Methyl | 6a | 78 | 7a | 48 |
| (CH$_3$CH$_2$CO)$_2$O | 3b | Ethyl | 6b | 78 | 7b | 44 |
| (CH$_3$CH$_2$CH$_2$CO)$_2$O | 3c | Propyl | 6c | 73 | 7c | 37 |
| [(CH$_3$)$_2$CHCO]$_2$O | 3d | Isopropyl | 6d | 78 | 7d | 40 |
| TBSO(CH2)$_4$COOSu | 3e | TBSO(CH$_2$)$_4$ | 6e | 68 | 7e | 50 |
|  | 3f |  | 6f | 91 | 7f | 25 |
|  | 3g |  | 6b | 79 | 7g | 48 |

TABLE 2-continued effect of bases on yields of compounds of series 4

| Base | Temp (° C.) | Yield (%)[a] |
|---|---|---|

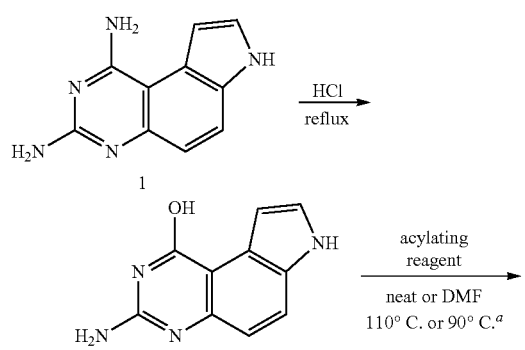

Example 3

Synthesis of N$^3$-Acylated Compounds of Series 7

[a] carried out with compound 5 (1.0 equivalents) and an anhydride used neat or an NHS ester (1.5 equivalents) in DMF

[b] carried out with compound 6 (1.0 equivalents) BOP (1.3 equivalents) and DBU (1.5 equivalents for four hours.) After that, 7N NH$_3$ in methanol was added.

Yields are isolated yields.

To achieve selective N$^3$ acylation, a more elaborate and indirect scheme was designed (Table 3). The N$^1$ amine was temporarily converted into a less nucleophilic hydroxyl group to give compounds of series 5 in quantitative yield through acid hydrolysis (Guan J et al, *Antimicrob Agents Chemother* 49, 4928-4933 (2005) and Trattner R B et al, *J Org Chem* 29, 2674-2677 (1964); both of which are incorporated by reference herein.) Then the nucleophilic N$^3$ in the compounds of series 5 were selectively acylated by treating with either an anhydride or NHS ester to provide compounds of series 6 in good to excellent yields (Table 3). The TBS ether was well tolerated and product 6e was obtained in 62% yield. Aromatic carboxylic NHS ester 3f was compatible with this acylation step and the desired compound 6f was generated in 56% yield. With the acylated intermediates of series 6 in hand, the N$^1$ amine was regenerated using an SNAr displacement reaction between ammonia (NH3/MeOH) and activated benzotriazole adducts generated between the compounds of series 6 and BOP (Wan Z K et al, *J Org Chem* 72, 10194-10210 (2007) to provide compounds 7a, 7b, 7c, 7d, 7e, 7f and 7g in moderate to good yields. Therefore, the hydroxyl group in 5 served as a temporary protecting group for the N$^1$ amine.

Example 4

Activity of Compounds of Series 4 and Series 7

The newly synthesized selectively mono-N-acylated compounds of series 4 and series 7 were evaluated as potential anticancer agents because compound 1 had been previously shown to display anticancer activity by inhibiting DHFR (Kuyper L F et al, *J Med Chem* 39, 892-903 (1996); incorporated by reference herein). Compounds of series 2 were not evaluated due to their poor solubility in DMSO. Two triple negative breast cancer (TNBC) cell lines (MDA-MB-231 and MDAMB-468) were selected to evaluate potential anticancer activity of the compounds of series 4 and series 7 by an MTT assay (Li B X et al, *Bioorg Med Chem* 20, 6811-6820 (2012); incorporated by reference herein.) TNBC represents a unique subtype of breast cancer clinically characterized by the lack of expression of estrogen receptor (ER), progesterone receptor (PR) and human epidermal growth factor receptor 2 (HER2). Subjects with triple negative breast cancer often have a poor prognosis (Kang S P et al, *Curr Opin Obstet Gynecol* 20, 40-46 (2008) and The Cancer Genome Atlas Network *Nature*, 490, 61-70 (2012); both of which are incorporated by reference herein). Current treatment options for TNBC are limited and novel agents are needed (Shastry M and Yardley D A, *Curr Opin Obstet Gynecol* 25, 40-48 (2013); incorporated by reference herein). The antiproliferative activity of compounds of series 4 and series 7 in MDA-MB-231 and MDAMB-468 cells is presented in Table 4.

TABLE 4

Antiproliferative activities of compounds of series 4 and series 7 in MDA-MB-231 and MDA-MG-468

| Compound | $GI_{50}$ (µM) | |
| --- | --- | --- |
|  | MDA-MB-231 | MDA-MB-468 |
| 1 | 4.13 ± 0.54 | 3.34 ± 0.93 |
| 4a | 32.62 ± 13.97 | 56.46 ± 17.97 |
| 4b | 18.66 ± 2.24 | 20.28 ± 7.40 |
| 4c | 26.86 ± 12.90 | 26.27 ± 7.40 |
| 4d | >100 | >100 |
| 4e | 15.64 ± 7.66 | 11.11 ± 1.73 |
| 4f | 8.46 ± 2.56 | 8.91 ± 1.28 |
| 7a | 27.17 ± 11.40 | 53.54 ± 29.54 |
| 7b | 21.43 ± 9.86 | 24.41 ± 3.33 |
| 7c | 25.52 ± 9.93 | 27.37 ± 4.52 |
| 7d | 39.66 ± 22.46 | 29.80 ± 8.41 |
| 7e | 2.43 ± 0.13 | 2.24 ± 0.40 |
| 7f | 1.60 ± 0.51 | 0.44 ± 0.14 |
| 7g | 0.65 ± 0.43 | 0.10 ± 0.079 |

$GI_{50}$ values represent the concentration that limits the growth of the cancer cells by 50% during a 72 hour incubation period. These are presented as mean±standard deviation of the mean of at least two independent experiments performed in duplicate.

Figure 2:
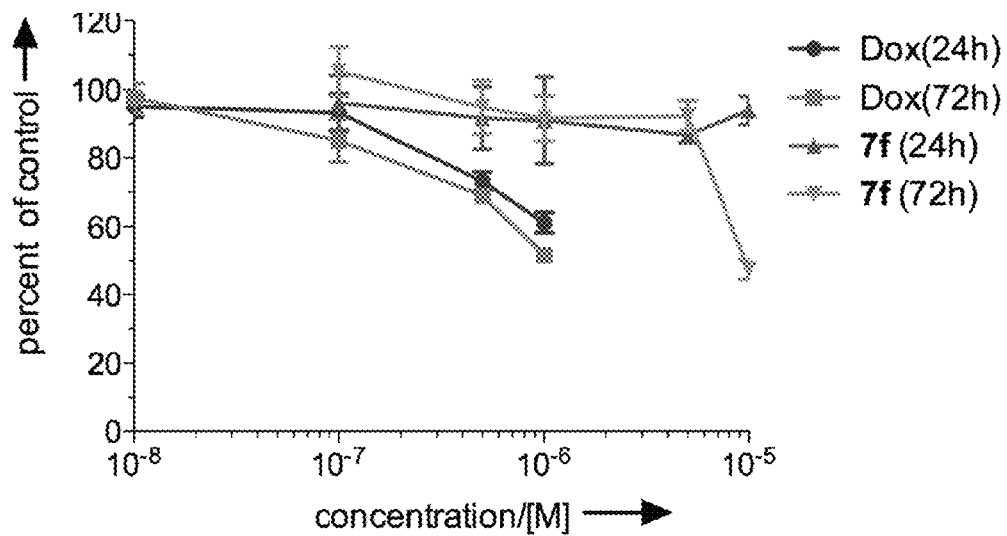
FIG. 2 is a plot showing the effect of compound 7f on normal human mammary epithelial cells (HMEC.) HMEC were treated with the indicated concentrations of doxorubicin or 7f for 24 or 72 hours as indicated. Cells treated for 24 hours were further incubated in drug free media for 48 hours. The number of viable cells was determined by an MTT assay.

In general, the compounds of series 7 are more potent than the compounds of series 4 (4d-4f vs 7d-7g). Although most of the compounds are less potent than the parent compound 1, compound 7f and 7g were more potent than compound 1 in both MDA-MB-231 ($GI_{50}$=1.60 µM) and MDA-MB-468 ($GI_{50}$=0.44 µM) cells. In addition, compound 7f was found to be not toxic to normal human mammary epithelial cells (HMEC) up to 5 µM after a 72-h incubation period (FIG. 2). This compares favorably to an approved cytotoxic chemotherapeutic agent such as doxorubicin (Dox). Dox has a $GI_{50}$=0.12 µM in MDA-MB-468 cells, but is toxic to normal HMEC cells at a concentration as low as 0.1 µM. These results indicate that 7f is a potential novel nontoxic anti-TNBC agent.

Figure 3:
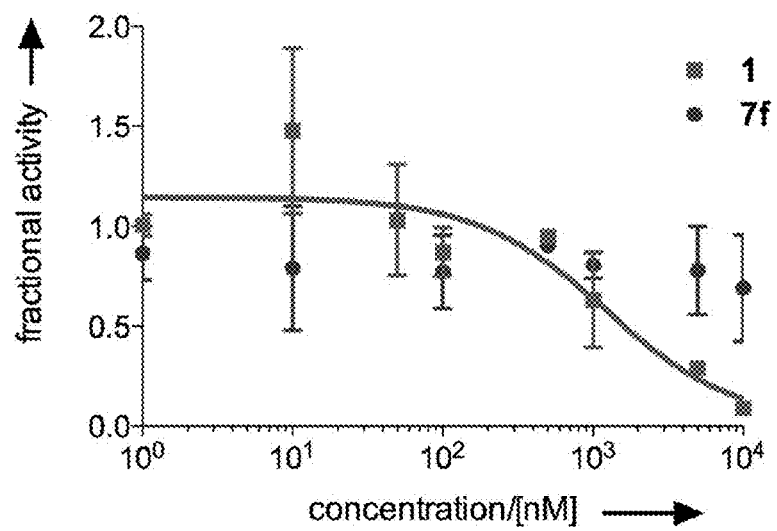
FIG. 3 is a plot showing the activity of compound 7f on human DHFR.

Compound 1 was known to be a human DHFR inhibitor based on the binding orientation of an N7-alkylated 1 in DHFR from *Candida albicans* and its structural similarity to human DHFR (Whitlow A J et al, *J Biol Chem* 272, 30289-30298 (1997); incorporated by reference herein). From that, it would be predicted that the bulky naphthyl group in compound 7f would not be accommodated in the human DHFR binding pocket. Indeed, it was found that 7f did not inhibit human DHFR up to a 10 µM concentration (FIG. 3). Therefore, the potent antiproliferative activity of 7f in TNBC cells is surprisingly independent of DHFR inhibition.

Figure 4:
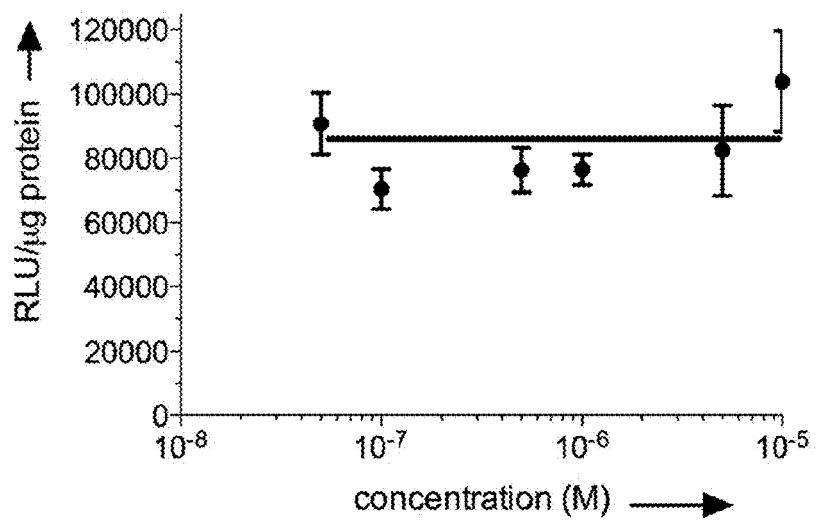
FIG. 4 is a plot showing the activity of compound 7f on CREB mediated gene transcription in HEK 293T cells. HEK 293T cells were transfected with a CREB renilla luciferase reporter (CRE-RLuc). Then the cells were treated with increasing concentrations of 7f for 30 min before the addition of forskolin at a final concentration of 10 µM. The cells were further incubated for 5 hours before cell lysis and renilla luciferase activity measurement. The renilla luciferase activity was normalized to the protein concentration of the cell lysates and was expressed as relative luciferase unit (RLU)/µg of proteins.

Other references show that small molecule inhibitors of CREB (cyclic-AMP response element binding protein) also have activity against cancer (Li B X et al 2012 supra and Xiao X et al, *Curr Cancer Drug Targets* 10, 384-391 (2010) which is incorporated by reference herein.) However, 7f was also unable to inhibit CREB-mediated gene transcription up to a 10 µM concentration using the CREB reporter assay in HEK 293T cells described in Li B X et al, *Chem Bio Chem* 10, 2721-2724 (2009) which is incorporated by reference herein (FIG. 4).

Example 5

Experimental Procedures

The solvents used for each reaction were purified from the Glass Contout solvent purification system. Melting points were determined in capillary tubes using MeI-Temp and are uncorrected. NMR spectra were recorded at 400 MHz ($^1$H NMR) and 100 MHz ($^{13}$C NMR). Chemical shifts (δ) are reported in ppm relative to the residual $CHCl_3$ (1H, 7.26 ppm, 13C, 77.0 ppm) or DMSO (1H, 2.50 ppm, 13C, 39.5 ppm). The following abbreviations were used to describe the splitting pattern of individual peaks if applicable: s=singlet, d=doublet, t=triplet, q=quartet, m=multiplet. The coupling constants (J) were reported in Hertz (Hz). Silica gel flash chromatography was performed using 230-400 mesh silica gel (EMD). The mass spectra were obtained from an LTQ Orbitrap Discovery mass spectrometer (Thermo Scientific, West Palm Beach, Fla.) with electrospray operated either in positive or negative mode. All final compounds were confirmed to be of >95% purity based on HPLC (Waters) analysis using an XBridge C18 column (4.6×150 mm) and detected at 254 nm (due to the poor solubility, compound 2a-2d were not evaluated by HPLC). The mobile phases for HPLC are water and acetonitrile, both of which contain 0.1% TFA (for compounds 2e, 4e, and 7e which contain a TBS group, 0.01% TFA was used due to instability of these compounds in 0.1% TFA).

In Vitro Human DHFR Inhibition:

The human DHFR assay was done with DHFR assay kit (Sigma) following the manufacturer's instructions with minor modifications. Different concentrations of a test compound were incubated with human DHFR (0.1875 mU) and NADPH (60 µM) in the 1× assay buffer for 2 min at room temperature. Then DHF (50 µM) was added to initiate the reduction reaction, which was immediately monitored by absorbance at 340 nm every 12 s for 3 min. The final reaction volume was 100 µL and the final DMSO concentration was 1%. The reaction velocities were calculated as the slopes from the absorbance-time curves.

MTT Assays:

TMTT assays for MDA-MB-231, MDA-MB-468 and HMEC were performed as described in Li et al, 2012 supra.

Inhibition of CREB-Mediated Gene Transcription:

Inhibition of CREB mediated transcription in HEK 293T cells by a CREB reporter assay was performed as described in Li and Xiao, 2009 supra.

Molecular Modeling:

Molecular modeling work was conducted in the Schrödinger modeling suite (Portland, Oreg.). The structures were optimized at HF/6-31G** level of theory in Jaguar. The structural minima were confirmed by the absence of any negative vibrational frequencies. The MEP surfaces were generated by mapping the electrostatic potentials onto the electron densities and were normalized from −50 kcal/mol to +50 kcal/mol.

Example 6

Synthesis of Compound 1

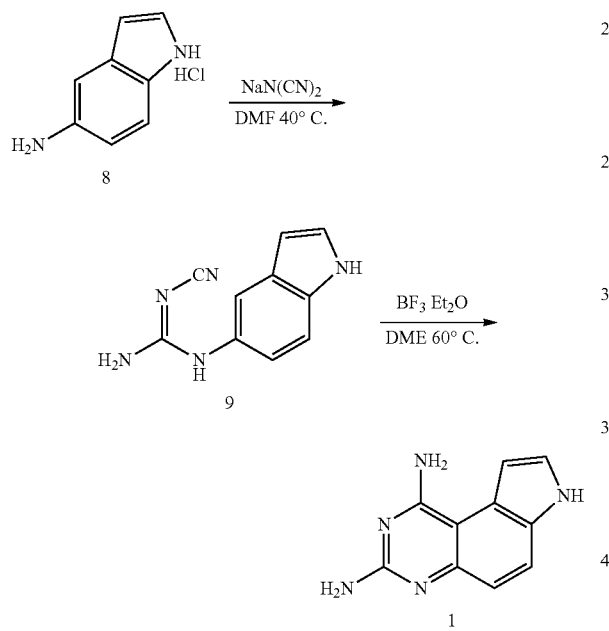

NaN(CN)$_2$ (7.3 g, 81.5 mmol) was added to a stirred solution of 8 (5.5 g, 32.6 mmol, prepared by treating a methanolic solution of 5-aminoindole with 1.5 equiv HCl in Et$_2$O) in DMF (55 mL). The reaction mixture was stirred at 40° C. for 4 hours. DMF was removed and the residue was treated with H$_2$O (50 mL) overnight. The gray solid was collected by filtration and dried in vacuum for 1 d to give compound 9 (6.3 g, 97% yield), which was used for the next step without further purification. The characterization data were consistent with literature reported values: 1H NMR (400 MHz, DMSO-d6) δ 11.12 (s, 1H), 8.86 (s, 1H), 7.46 (s, 1H), 7.35-7.33 (m, 2H), 6.94 (dd, J=8.8 Hz, 2.0 Hz, 1H), 6.74 (s, 2H), 6.40 (s, 1H). Boron trifluoride (18.8 mL, 152 mmol) was added dropwise to a stirred suspension of 9 (6.3 g, 31.6 mmol) in DME (600 mL) at 60° C. The resulting mixture was stirred at 60° C. for 4 h. Then the solvent was removed and the residue was suspended in MeOH (60 mL) and treated with NH$_4$OH (40 mL) for 2 h. The solvents were removed in vacuo and the residue was purified by column chromatography on silica gel, eluting with 3:1 DCM:MeOH with 1% NH4OH to give a yellow solid, which was treated with 1 N NaOH (50 mL) at room temperature for overnight. Then the solid was collected to give compound 1 as a white to pale yellow solid (5.2 g, 89% yield). The characterization data were consistent with literature reported values: $^1$H NMR (400 MHz, DMSO-d6) δ 11.55 (s, 1H), 7.64 (d, J=8.8 Hz, 1H), 7.43 (t, J=2.8 Hz, 1H), 7.03-7.00 (m, 2H), 6.65 (brs, 2H), 5.65 (s, 2H); 13C NMR (100 MHz, DMSO-d6) δ 162.0, 159.1, 150.1, 130.4, 124.8, 120.0, 119.1, 119.0, 102.5, 102.0.

Example 7

Common Procedure for N$^7$ Acylation

The following reaction shows the common reaction for the synthesis of compounds of series 2, detailed in Examples 8-13 below. For acylating reagents see Table 1 above.

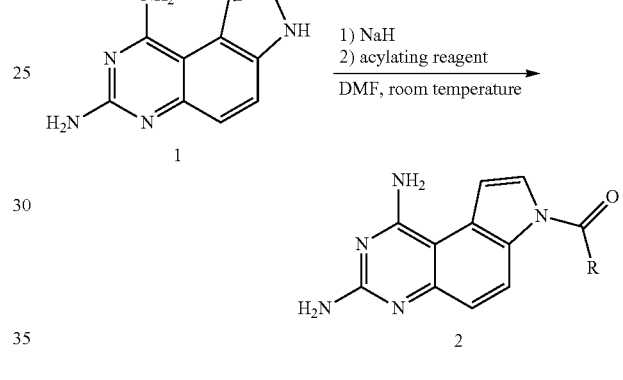

Example 8

Synthesis of Compound 2a

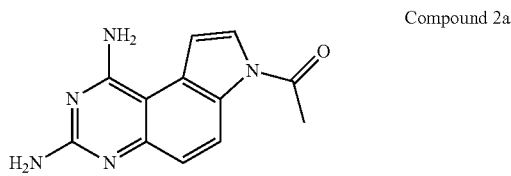 [SMILES: CC(=O)n1ccc2c3c(N)nc(N)nc3ccc21]

Compound 2a

NaH (20.0 mg, 60% in mineral oil, 0.50 mmol) was added to a stirred solution of compound 1 (90.0 mg, 0.45 mmol) in dry DMF (5 mL) at 25° C. under an Ar atmosphere. The reaction mixture was stirred for 1 h, when Ac$_2$O (47.3 μl, 0.50 mmol) was added and the mixture was stirred for another 3 h. The solvent was removed and the residue was treated with water. The solid was collected by filtration and dried in vacuum. Then it was treated with DCM (2 mL) and collected by filtration to give the desired product 2a as a yellowish solid (85.0 mg, 78% yield): mp 202-204° C. 1H NMR (400 MHz, DMSO-d6) δ 8.56 (d, J=8.8 Hz, 1H), 7.99 (d, J=3.6 Hz, 1H), 7.39 (d, J=4.0 Hz, 1H), 7.18 (d, J=9.2 Hz, 1H), 6.90 (s, 2H), 5.92 (s, 2H), 2.69 (s, 3H); HRMS (ESI) Calcd for C$_{12}$H$_{12}$N$_5$O$^+$ (M+H)+ 242.10364. Found 242.10313.

Example 9

Synthesis of Compound 2b

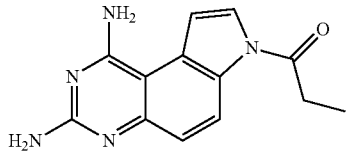

Compound 2b

From 20.0 mg (0.10 mmol) of compound 1, compound 2b (20.0 mg, 78% yield) was obtained as a yellowish solid: mp 210-212° C.; 1H NMR (400 MHz, DMSO-d6) δ 8.59 (d, J=9.2 Hz, 1H), 8.03 (d, J=3.6 Hz, 1H), 7.39 (d, J=4.0 Hz, 1H), 7.18 (d, J=9.2 Hz, 1H), 6.90 (s, 2H), 5.92 (s, 2H), 3.12 (q, J=7.2 Hz, 2H), 1.19 (t, J=7.6 Hz, 3H); HRMS (ESI) Calcd for $C_{13}H_{14}N_5O^+$ (M+H)+ 256.11929. Found 256.11893.

Example 10

Synthesis of Compound 2c

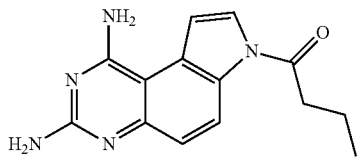

Compound 2c

From 65.0 mg (0.33 mmol) of 1, compound 2c (65.0 mg, 73% yield) was obtained as a yellowish solid: mp 196-198° C.; 1H NMR (400 MHz, DMSO-d6) δ 8.59 (d, J=9.2 Hz, 1H), 8.05 (d, J=3.6 Hz, 1H), 7.39 (d, J=4.0 Hz, 1H), 7.18 (d, J=8.8 Hz, 1H), 6.90 (brs, 2H), 5.92 (s, 2H), 3.07 (t, J=7.2 Hz, 2H), 1.73 (sextet, J=7.2 Hz, 2H), 0.99 (t, J=7.2 Hz, 3H); HRMS (ESI) Calcd for C14H16N5O+ (M+H)+ 270.13494. Found 270.13507.

Example 11

Synthesis of Compound 2d

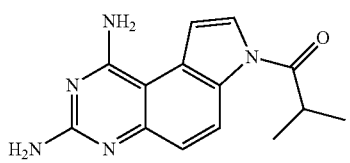

Compound 2d

From 20.0 mg (0.10 mmol) of 1, compound 2d (21.0 mg, 78% yield) was obtained as a yellowish solid: mp 200-202° C. 1H NMR (400 MHz, DMSO-d6) δ 8.59 (d, J=9.2 Hz, 1H), 8.14 (d, J=4.0 Hz, 1H), 7.41 (d, J=3.6 Hz, 1H), 7.18 (d, J=9.2 Hz, 1H), 6.90 (s, 2H), 5.92 (s, 2H), 3.63 (septet, J=6.8 Hz, 1H), 1.24 (d, J=6.8 Hz, 6H); 13C NMR (100 MHz, DMSO-d6) δ 176.5, 162.3, 160.0, 151.5, 129.4, 126.5, 124.0, 122.2, 121.8, 108.1, 102.6, 32.9, 19.6; HRMS (ESI) Calcd for $C_{14}H_{16}N_5O^+$ (M+H)+ 270.13494. Found 270.13498.

Example 12

Synthesis of Compound 2e

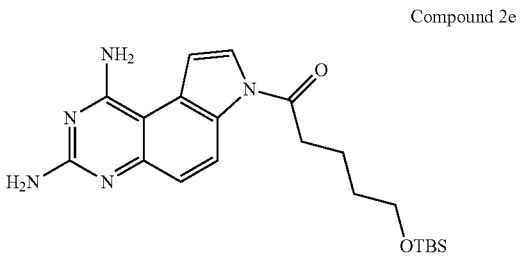 [SMILES: CC(C)(C)[Si](C)(C)OCCCCC(=O)n1ccc2c3c(N)nc(N)nc3ccc21]

Compound 2e

DCC (262 mg, 1.27 mmol) was added to a stirred solution of 5-(tert-Butyldimethylsilyloxy)pentanoic acid (247 mg, 1.06 mmol), NHS (146 mg, 1.27 mmol) and DMAP (14 mg, 0.117 mmol) in dry THF (5 mL) at 0° C. The resulting mixture was stirred for 24 h at room temperature. The solid was filtered off and the solvent was removed in vacuo. The residue was purified by column chromatography on silica gel, eluting with 2:1 Hexane:EtOAc to give 3e (280 mg, 80% yield) as a colorless oil: 1H NMR (400 MHz, CDCl3) δ 3.64 (t, J=6.4 Hz, 2H), 2.84-2.83 (m, 4H), 2.64 (t, J=7.6 Hz, 2H), 1.85-1.78 (m, 2H), 1.65-1.58 (m, 2H), 0.88 (s, 9H), 0.04 (s, 6H); 13C NMR (100 MHz, CDCl$_3$) δ 169.3, 168.8, 62.5, 31.8, 30.8, 26.1, 25.7, 21.4, 18.4, -5.2; HRMS (ESI) Calcd for $C_{15}H_{28}NO_5Si^+$ (M+H)$^+$ 330.17313. Found 330.17282. From 100 mg (0.50 mmol) of 1, following the representative procedure above, however, carboxylic NHS ester TBSO(CH$_2$)$_4$COOSu 3e was used instead of anhydride and when the reaction was complete, the solvent was removed and the residue was purified by column chromatography on silica gel, eluting with THF to give the desired compound 2e (135 mg, 65% yield) as a yellowish solid: mp 173-175° C. 1H NMR (400 MHz, DMSO-d6) δ 8.58 (d, J=9.2 Hz, 1H), 8.04 (d, J=4.0 Hz, 1H), 7.39 (d, J=4.0 Hz, 1H), 7.18 (d, J=9.2 Hz, 1H), 6.92 (brs, 2H), 5.94 (s, 2H), 3.64 (t, J=6.4 Hz, 2H), 3.11 (t, J=6.8 Hz, 2H), 1.78-1.72 (m, 2H), 1.65-1.55 (m, 2H), 0.86 (s, 9H), 0.03 (s, 6H); 13C NMR (100 MHz, DMSO-d6) δ 172.5, 162.2, 159.9, 151.4, 129.3, 126.6, 123.9, 122.0, 121.7, 107.8, 102.7, 62.3, 34.6, 31.6, 25.9, 20.8, 18.0, -5.3; HRMS (ESI) Calcd for $C_{21}H_{32}N_5O_2Si^+$ (M+H)$^+$ 414.23198. Found 414.23187.

Example 13

Synthesis of Compound 2f

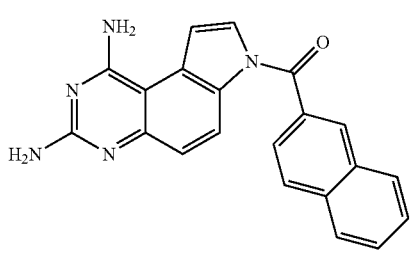

Compound 2f

NHS (748 mg, 6.5 mmol) and EDCl.HCl (1.25 g, 6.5 mmol) was added to a stirred solution of 2-naphthoic acid (861 mg, 5.0 mmol) in dry DMF (8 mL). The resulting mixture was stirred overnight. Then the solvent was removed and the residue was treated with $H_2O$ (15 mL). The white solid was collected by filtration to give compound 3f (1.31 g, 97% yield): mp 148-150° C. 1H NMR (400 MHz, DMSO-d6) δ 8.87 (s, 1H), 8.25 (d, J=8.4 Hz, 1H), 8.17 (d, J=8.8 Hz, 1H), 8.09 (d, J=8.4 Hz, 1H), 8.04 (d, J=8.4 Hz, 1H), 7.78 (t, J=7.6 Hz, 1H), 7.70 (t, J=7.2 Hz, 1H), 2.93 (s, 4H). 13C NMR (100 MHz, DMSO-d6) δ 170.5, 162.0, 135.9, 132.5, 132.0, 130.0, 129.8, 129.4, 128.0, 127.7, 124.5, 121.7, 25.6. From 100 mg (0.50 mmol) of 1, following the representative procedure above, however, carboxylic NHS ester succinimidyl 2-naphthoate 3f was used instead of anhydride. Compound 2f (160 mg, 91% yield) was obtained as a yellowish solid: mp 188-190° C. 1H NMR (400 MHz, DMSO-d6) δ 8.50 (d, J=9.2 Hz, 1H), 8.43 (s, 1H), 8.16-8.13 (m, 2H), 8.08 (d, J=8.0 Hz, 1H), 7.87 (d, J=8.8 Hz, 1H), 7.72 (t, J=8.0 Hz, 1H), 7.67 (t, J=7.6 Hz, 1H), 7.61 (d, J=3.6 Hz, 1H), 7.44 (d, J=3.2 Hz, 1H), 7.25 (d, J=9.2 Hz, 1H), 6.94 (s, 2H), 5.98 (s, 2H); 13C NMR (100 MHz, DMSO-d6) δ 168.5, 162.3, 160.0, 151.6, 134.5, 131.9, 131.0, 130.6, 129.8, 129.3, 128.7, 128.6, 128.5, 127.9, 127.3, 125.5, 124.4, 122.0, 121.5, 108.2, 102.7; HRMS (ESI) Calcd for $C_{21}H_{16}N_5O^+$ $(M+H)^+$ 354.13494. Found 354.13490.

Example 14

Common Procedure for $N^1$ Acylation Reaction

The following reaction shows the common reaction for the synthesis of compounds of series 4, detailed in Examples 15-20 below. Method A and method B for each compound are described in the corresponding example.

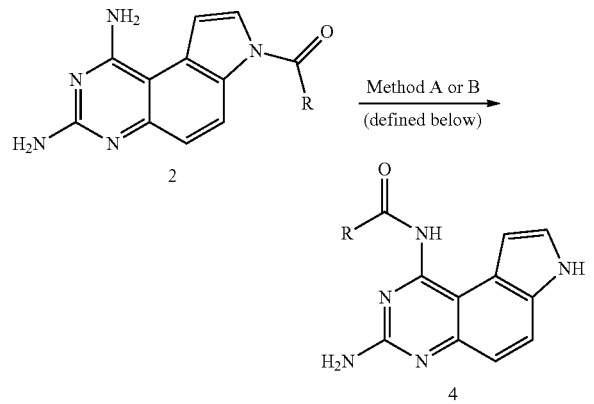

Example 15

Synthesis of Compound 4a

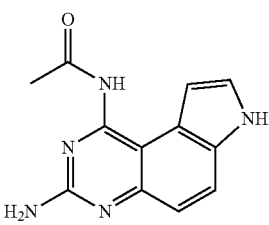

Compound 4a

Method A: NaH (6.0 mg, 0.15 mmol) was added to a stirred suspension of compound 2a (33 mg, 0.137 mmol) in dry DMF (3 mL) under argon atmosphere at 25° C. The reaction mixture was stirred at 25° C. for 2 h, when a few drops of water was added to quench the reaction. Then the solvents were removed and the residue was purified by column chromatography on silica gel, eluting with 15:1 DCM:MeOH containing 1% DIPEA to give a sticky solid, which was treated with water (1 mL) at room temperature for 1 hour. Then the solid was collected by filtration to give the desired product 4a (8.0 mg, 23% yield) as a yellowish solid: mp 236-238° C. 1H NMR (400 MHz, DMSO-d6) δ 11.61 (s, 1H), 10.22 (s, 1H), 7.80 (d, J=8.8 Hz, 1H), 7.43 (brs, 1H), 7.17 (d, J=8.8 Hz, 1H), 6.70 (brs, 1H), 6.38 (s, 2H), 2.20 (s, 3H); 13C NMR (100 MHz, DMSO-d6) δ 169.7, 159.0, 157.0, 152.1, 130.6, 124.8, 121.2, 119.9, 118.8, 109.2, 103.5, 23.5; HRMS (ESI) Calcd for $C_{12}H_{12}N_5O^+$ $(M+H)^+$ 242.10364. Found 242.10361.

Method B: A suspension of compound 2a (40 mg, 0.166 mmol) in dry DMF under Ar was cooled to 0° C. LiHMDS (182 μl, 1M, 0.182 mmol) was added dropwise to the suspension. The reaction mixture was stirred for 40 min at 0° C. and then a few drops of water were added to quench the reaction. Then the solvents were removed in vacuo and the residue was purified by column chromatography on silica gel, eluting with 15:1 DCM:MeOH containing 1% DIPEA to give compound 4a (18 mg, 45% yield) as a yellowish solid.

Example 16

Synthesis of Compound 4b

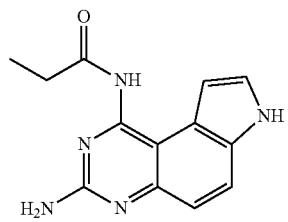

Compound 4b

Method A. From 53.0 mg (0.21 mmol) of 2b, and after column chromatography on silica gel, eluting with 15:1 DCM:MeOH containing 1% DIPEA, compound 4b (17.0 mg, 32% yield) was obtained as a yellowish solid: mp 226-228° C. 1H NMR (400 MHz, DMSO-d6) δ 11.59 (s, 1H), 10.19 (s, 1H), 7.80 (d, J=8.8 Hz, 1H), 7.42 (t, J=2.8 Hz, 1H), 7.17 (d, J=8.8 Hz, 1H), 6.68 (brs, 1H), 6.39 (s, 2H), 2.53 (q, J=7.6 Hz, 2H), 1.12 (t, J=7.6 Hz, 3H); 13C NMR (100 MHz, DMSO-d6) δ 173.1, 159.1, 157.1, 152.1, 130.6, 124.8, 121.2, 119.9, 118.8, 109.3, 103.6, 29.0, 9.4; HRMS (ESI) Calcd for $C_{13}H_{14}N_5O^+$ $(M+H)^+$ 256.11929. Found 256.11941.

Example 17

Synthesis of Compound 4c

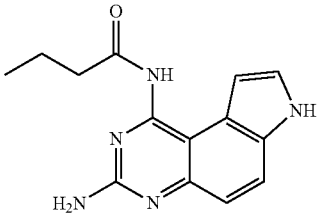

Compound 4c

Method A. From 47.0 mg (0.175 mmol) of 2c, and after column chromatography on silica gel, eluting with 15:1 DCM:MeOH containing 1% DIPEA, compound 4c (15.0 mg, 32% yield) was obtained as a yellowish solid: mp 224-226° C. 1H NMR (400 MHz, DMSO-d6) δ 11.59 (s, 1H), 10.17 (s, 1H), 7.80 (d, J=8.8 Hz, 1H), 7.42 (t, J=2.8 Hz, 1H), 7.17 (d, J=8.8 Hz, 1H), 6.70 (brs, 1H), 6.36 (s, 2H), two protons were buried in residual DMSO signal, 1.65 (sextet, J=7.6 Hz, 2H), 0.96 (t, J=7.2 Hz, 3H); 13C NMR (100 MHz, DMSO-d6) δ 172.2, 159.1, 157.1, 152.1, 130.6, 124.7, 121.2, 119.9, 118.8, 109.4, 103.6, 37.7, 18.2, 13.9; HRMS (ESI) Calcd for $C_{14}H_{16}N_5O^+$ (M+H)$^+$, 270.13494. Found 270.13497.

Example 18

Synthesis of Compound 4d

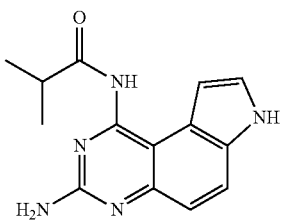

Compound 4d

Method A. From 52.0 mg (0.193 mmol) of compound 2d, and after column chromatography on silica gel, eluting with 10:1 DCM:MeOH containing 1% DIPEA, compound 4d (15.0 mg, 27% yield) was obtained as a yellowish solid: mp 232-234° C. 1H NMR (400 MHz, DMSO-d6) δ 11.59 (s, 1H), 10.21 (s, 1H), 7.80 (d, J=9.2 Hz, 1H), 7.43 (t, J=2.8 Hz, 1H), 7.17 (d, J=9.2 Hz, 1H), 6.70 (brs, 1H), 6.41 (s, 2H), 2.85 (septet, J=6.8 Hz, 1H), 1.18 (d, J=7.2 Hz, 6H); 13C NMR (100 MHz, DMSO-d6) δ 175.9, 159.1, 157.3, 152.2, 130.6, 124.7, 121.2, 119.9, 118.8, 109.7, 103.6, 34.3, 19.3;

HRMS (ESI) Calcd for $C_{14}H_{16}N_5O^+$ (M+H)$^+$, 270.13494. Found 270.13467.

Example 19

Synthesis of Compound 4e

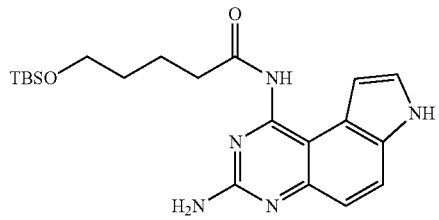

Compound 4e

Method A. From 261 mg (0.631 mmol) of 2e, and after column chromatography on silica gel, eluting with 20:1 DCM:MeOH containing 1% DIPEA, compound 4e (100 mg, 38% yield) was obtained as a yellowish solid: mp 172-174° C. 1H NMR (400 MHz, DMSO-d6) δ 11.61 (s, 1H), 10.23 (s, 1H), 7.82 (d, J=9.2 Hz, 1H), 7.42 (s, 1H), 7.17 (d, J=8.8 Hz, 1H), 6.70 (s, 1H), 6.48 (brs, 2H), 3.61 (t, J=6.0 Hz, 2H), two protons were buried in residual DMSO signal, 1.73-1.62 (m, 2H), 1.58-1.52 (m, 2H), 0.86 (s, 9H), 0.03 (s, 6H); 13C NMR (100 MHz, DMSO-d6) δ 172.3, 159.1, 157.1, 152.2, 130.7, 124.7, 121.3, 120.0, 118.9, 109.4, 103.6, 62.3, 35.5, 32.0, 25.9, 21.3, 18.0, −5.2; HRMS (ESI) Calcd for C21H32N5O2Si+ (M+H)+ 414.23198. Found 414.23145.

Example 20

Synthesis of Compound 4f and 4f'

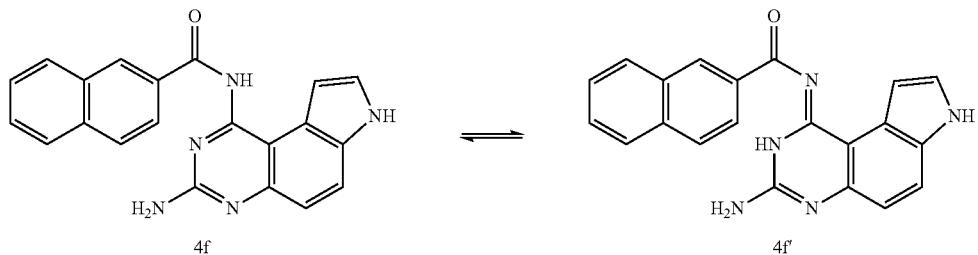

Compound 4f and 4f'

Method B. From 80 mg (0.226 mmol) of 2f, and after column chromatography on silica gel, eluting with 20:1 DCM:MeOH containing 1% DIPEA, a yellow solid was obtained (40 mg, 50% yield), which exists as a 1:1 tautomeric mixture of 4f and 4f' in DMSO-d6: mp 230-232° C. 1H NMR (400 MHz, DMSO-d6) δ 14.37 (s, 1H), 11.64 (s, 1H), 11.57 (s, 1H), 11.11 (s, 1H), 8.93 (s, 1H), 8.78 (s, 1H), 8.44 (d, J=8.4 Hz, 1H), 8.14-8.02 (m, 7H), 7.87-7.83 (m, 2H), 7.78 (brs, 1H), 7.71-7.62 (m, 5H), 7.30 (brs, 1H), 7.25-7.23 (m, 3H), 7.09 (d, J=8.4 Hz, 1H), 6.57 (s, 1H), 6.50 (s, 2H); 13C NMR (100 MHz, DMSO-d6) δ 177.7, 166.4, 159.3, 158.7, 157.8, 152.3, 149.7, 148.4, 135.8, 134.7, 132.4, 131.6, 131.2, 130.7, 129.7, 129.3, 128.8, 128.4, 128.2, 127.9, 127.8, 127.0, 126.7, 126.3, 125.6, 125.0, 124.4, 123.0, 121.5, 120.1, 118.9, 118.5, 110.6, 107.7, 105.4, 103.4; HRMS (ESI) Calcd for $C_{21}H_{32}N_5O_2Si^+$ (M+H)$^+$ 354.13494. Found 354.13475. When a mixture of 4f and 4f' in DMSO-d6 (375 μl) was treated with aq. NaOH (125 µl, 0.4 N), it became 4f and all the active protons disappeared due to the H-D exchange: 1H NMR (400 MHz) 8.61 (s, 1H), 8.33 (dd, J=8.4 Hz, 1.2 Hz, 1H), 7.97-7.86 (m, 3H), 7.64 (d, J=8.8 Hz, 1H), 7.53-7.48 (m, 2H), 7.15 (d, J=2.8 Hz, 1H), 7.00 (d, J=2.4 Hz, 1H), 6.94 (d, J=8.8 Hz, 1H); 13C NMR (100 MHz) 171.6, 166.6, 159.2, 148.9, 139.4, 134.1, 133.6, 133.2, 129.3, 128.4, 128.1, 127.4, 127.3, 127.1, 126.6, 123.6, 120.7, 117.0, 110.9, 104.9.

Example 21

Synthesis of Intermediate Compound 5 from Compound 1

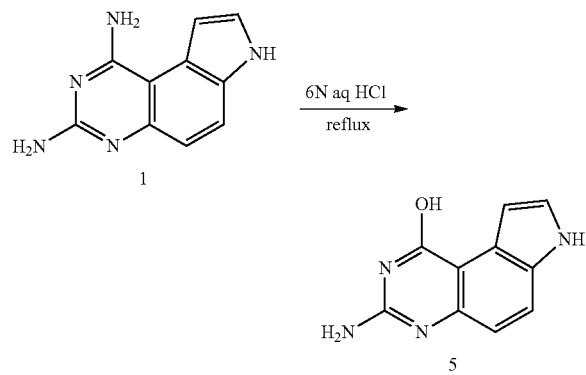

A suspension of compound 1 (200 mg, 1.0 mmol) in 6 N aq. HCl (10.0 mL) was heated under reflux overnight. The reaction mixture was adjusted to pH=10-11 with 10.0 N NaOH and the resulting black solution was stirred for 1 hour. Then the pH was adjusted to between 6 and 7 and the precipitate was collected by filtration to give the desired product 5 (200 mg, 99% yield) as a brown solid: mp 284-286° C.; 1H NMR (400 MHz, DMSO-d6) δ 11.34 (s, 1H), 10.95 (brs, 1H), 7.64 (d, J=8.8 Hz, 1H), 7.41 (t, J=2.4 Hz, 1H), 7.10 (s, 1H), 6.97 (d, J=8.4 Hz, 1H), 6.17 (s, 2H); 13C NMR (100 MHz, DMSO-d6) δ 162.7, 150.9, 142.9, 131.8, 127.0, 123.9, 119.2, 115.2, 107.6, 102.5; HRMS (ESI) Calcd for $C_{10}H_9N_4O^+$ (M+H)$^+$ 201.07709. Found 201.07708.

Example 22

Common Procedure for the Reaction of Compound 5 with Anhydride or Carboxylic NHS Ester to Prepare N3 Acylated Intermediates of Series 6

The following reaction shows the common reaction for the synthesis of intermediate compounds of series 6, detailed in Examples 23-28 below.

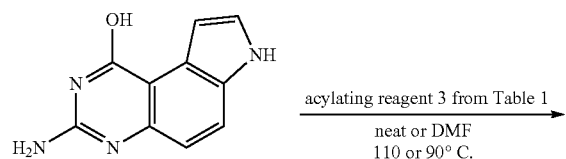

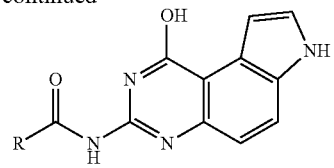

Example 23

Synthesis of Intermediate Compound 6a

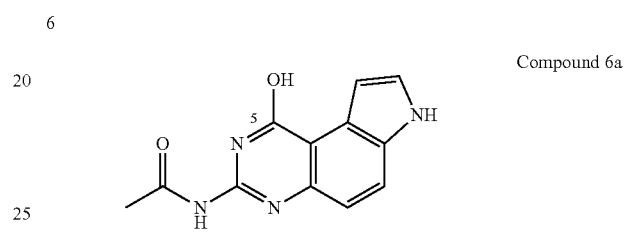

A suspension of compound 5 (50 mg, 0.25 mmol) in Ac$_2$O (3 mL) was stirred at 110° C. for 1.5 h. The reaction mixture was cooled to room temperature. The excess of acetic anhydride was removed and the residue was treated with DCM (3 mL). The solid was collected by filtration to give the desired product 6a (50 mg, 83% yield) as a brown solid, which was used for the next step without further purification: mp 266-268° C. 1H NMR (400 MHz, DMSO-d6) δ 11.95 (s, 1H), 11.61 (s, 1H), 11.49 (s, 1H), 7.83 (d, J=8.4 Hz, 1H), 7.55 (t, J=2.8 Hz, 1H), 7.23-7.20 (m, 2H), 2.17 (s, 3H); 13C NMR (100 MHz, DMSO-d6) δ 173.4, 160.4, 144.8, 144.7, 132.8, 127.3, 123.7, 119.6, 119.0, 111.1, 103.0, 23.8; HRMS (ESI) Calcd for $C_{12}H_9N_4O_2$ (M−H)$^-$ 241.07310. Found 241.07294.

Example 24

Synthesis of Intermediate Compound 6b

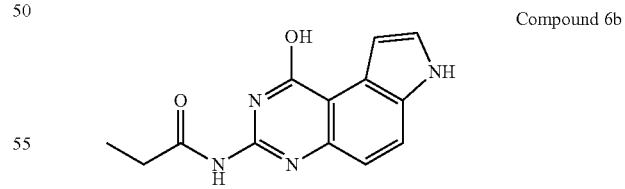

From 30 mg of compound 5, compound 6b (32 mg, 84% yield) was obtained as a brown solid: mp 262-264° C. 1H NMR (400 MHz, DMSO-d6) δ 12.01 (s, 1H), 11.58 (s, 1H), 11.46 (s, 1H), 7.83 (d, J=8.8 Hz, 1H), 7.55 (t, J=2.4 Hz, 1H), 7.26-7.18 (m, 2H), 2.47 (q, J=7.2 Hz, 2H), 1.09 (t, J=7.6 Hz, 3H); 13C NMR (100 MHz, DMSO-d6) δ 176.9, 160.4, 144.9, 144.8, 132.7, 127.3, 123.7, 119.6, 119.0, 111.1, 103.0, 29.4, 8.9; HRMS (ESI) Calcd for $C_{13}H_{13}N_4O_2$+ (M+H)$^+$ 257.10330. Found 257.10318.

Example 25

Synthesis of Intermediate Compound 6c

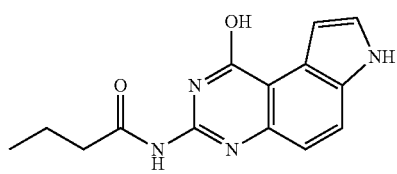

Compound 6c

From 35 mg of compound 5, compound 6c (40 mg, 85% yield) was obtained as a brown solid: mp 270-272° C. 1H NMR (400 MHz, DMSO-d6) δ 12.01 (s, 1H), 11.65 (s, 1H), 11.45 (s, 1H), 7.83 (d, J=9.2 Hz, 1H), 7.55 (t, J=2.4 Hz, 1H), 7.26-7.21 (m, 2H), 2.44 (t, J=7.6 Hz, 2H), 1.63 (sextet, J=7.2 Hz, 2H), 0.93 (t, J=7.2 Hz, 3H); 13C NMR (100 MHz, DMSO-d6) δ 176.1, 160.4, 144.9, 144.8, 132.8, 127.3, 123.7, 119.6, 119.0, 111.1, 103.0, 37.9, 18.1, 13.5; HRMS (ESI) Calcd for $C_{14}H_{15}N_4O_2^+$ (M+H)$^+$ 271.11895. Found 271.11874.

Example 26

Synthesis of Intermediate Compound 6d

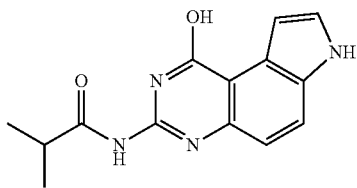

Compound 6d

From 30 mg of compound 5, compound 6d (27 mg, 67% yield) was obtained as a brown solid: mp 240-242° C. 1H NMR (400 MHz, DMSO-d6) δ 12.01 (s, 1H), 11.65 (s, 1H), 11.45 (s, 1H), 7.84 (d, J=8.8 Hz, 1H), 7.55 (t, J=2.8 Hz, 1H), 7.28-7.20 (m, 2H), 2.77 (septet, J=7.2 Hz, 1H), 1.13 (d, J=7.2 Hz, 6H); 13C NMR (100 MHz, DMSO-d6) δ 180.1, 160.3, 145.0, 144.8, 132.8, 127.3, 123.7, 119.5, 119.0, 111.1, 103.0, 34.8, 19.0; HRMS (ESI) Calcd for $C_{14}H_{15}N_4O_2^+$ (M+H)$^+$, 271.11895. Found 271.11881.

Example 27

Synthesis of Intermediate Compound 6e

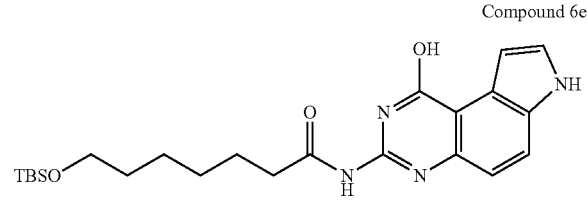 [SMILES: CC(C)(C)[Si](C)(C)OCCCCCCC(=O)Nc1nc(O)c2c(ccc3[nH]ccc32)n1]

Compound 6e

A mixture of compound 5 (100.0 mg, 0.5 mmol) and compound 3e (247 mg, 0.75 mmol) in dry DMF (5 mL) was stirred at 90° C. for 4 h. Then the solvent was removed and the residue was purified by column chromatography on silica gel, eluting with 2:1 DCM:EtOAc containing 1% DIPEA to give compound 6e, which was further washed with Et$_2$O (3 mL) to give the desired compound as a white solid (130 mg, 62% yield): mp 188-190° C. 1H NMR (400 MHz, DMSO-d6) δ 12.0 (s, 1H), 11.6 (s, 1H), 11.5 (s, 1H), 7.83 (d, J=8.8 Hz, 1H), 7.55 (brs, 1H), 7.23-7.21 (m, 2H), 3.60 (t, J=6.0 Hz, 2H), 2 protons were buried in residual DMSO signal, 1.70-1.60 (m, 2H), 1.55-1.45 (m, 2H), 0.86 (s, 9H), 0.03 (s, 6H); 13C NMR (100 MHz, DMSO-d6) δ 176.2, 160.4, 144.9, 144.8, 132.8, 127.3, 123.7, 119.6, 119.0, 111.1, 103.0, 62.1, 35.7, 31.6, 25.9, 21.0, 18.0, −5.2; HRMS (ESI) Calcd for $C_{21}H_{31}N_4O_3Si^+$ (M+H)$^+$ 415.21599. Found 415.21555.

Example 28

Synthesis of Intermediate Compound 6f

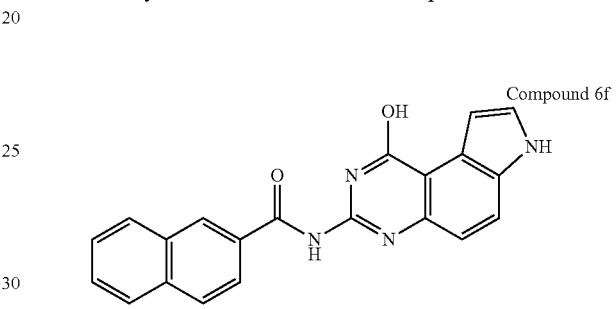

Compound 6f

Following the same procedure as that described for 6e. From 40 mg of 5, and after column chromatography on silica gel, eluting with 3:1 EtOAc:DCM containing 1% DIPEA, compound 6f (40 mg, 67% yield) was obtained as a yellowish solid: mp 226-228° C. 1H NMR (400 MHz, DMSO-d6) δ 12.5 (brs, 1H), 11.9 (brs, 1H), 11.7 (s, 1H), 8.8 (s, 1H), 8.16 (d, J=8.0 Hz, 1H), 8.10-8.01 (m, 3H), 7.89 (d, J=8.8 Hz, 1H), 7.69-7.60 (m, 3H), 7.34 (d, J=8.4 Hz, 1H), 7.25 (s, 1H); 13C NMR (100 MHz, DMSO-d6) δ 160.7, 134.8, 132.9, 132.1, 129.7, 129.4, 128.4, 128.0, 127.9, 127.7, 127.0, 124.8, 123.9, 119.8, 102.9; HRMS (ESI) Calcd for $C_{21}H_{15}N_4O_2^+$ (M+H)$^+$ 355.11895. Found 355.11893.

Example 29

Synthesis of Compound 6g

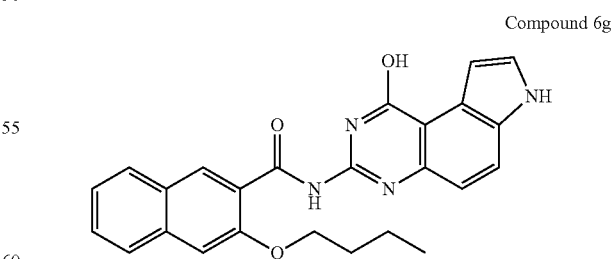

Compound 6g

Synthesis of 3-Butoxy-N-(1-hydroxy-7H-pyrrolo[3,2-f]quinazolin-3-yl)-2-naphthamide (6g)

From 100 mg of 5, 6g was obtained as a yellow solid (168 mg, 79% yield). mp 280-282° C. $^1$H NMR (400 MHz, DMSO-$d_6$) δ 12.06 (s, 1H), 11.67 (s, 1H), 11.37 (s, 1H), 8.48 (s, 1H), 8.03 (d, J=8.4 Hz, 1H), 7.90 (d, J=8.4 Hz, 1H), 7.87 (d, J=8.8 Hz, 1H), 7.62-7.57 (m, 3H), 7.47-7.43 (m, 1H), 7.26-7.24 (m, 2H), 4.28 (t, J=6.0 Hz, 2H), 1.90 (quintet, J=6.0 Hz, 2H), 1.62 (sextet, J=7.2 Hz, 2H), 1.01 (t, J=7.2 Hz, 3H). $^{13}$C NMR (100 MHz, DMSO-$d_6$) δ 167.1, 160.4, 153.5, 144.6, 144.3, 136.0, 132.9, 132.0, 128.9, 128.8, 127.4, 127.3, 126.5, 124.7, 123.7, 122.5, 119.6, 119.2, 111.3, 107.9, 103.7, 68.8, 30.8, 19.1, 13.9.

Example 30

Common Procedure for the Synthesis of N3 Acylated Compounds of Series 7 from Intermediate Compounds of Series 6

The following reaction shows the common reaction for the synthesis of compounds of series 7, detailed in Examples 30-35 below.

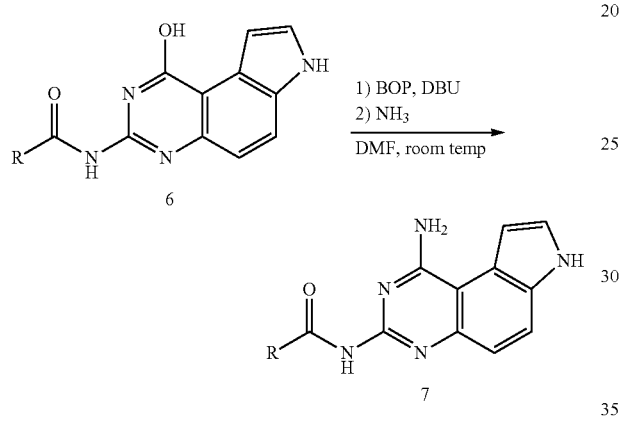

Example 31

Synthesis of Compound 7a

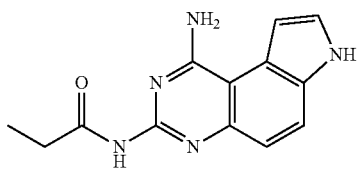

Compound 7a

BOP (83.1 mg, 0.188 mmol) and DBU (32.3 μl, 0.216 mmol) were added to a stirred solution of 6a (35.0 mg, 0.144 mmol) in dry DMF (3 mL). The resulting reaction mixture was stirred for 4 h, when NH3 (7 N in MeOH, 0.82 mL, 5.7 mmol) was added. The reaction mixture was stirred at 25° C. for 16 h. The solvents were removed and the residue was purified by column chromatography on silica gel, eluting with 1.5:1 EtOAc:THF containing 1% DIPEA to give a yellow solid, which was further treated with DCM (2 mL) and collected by filtration to give the desired compound 7a (17.0 mg, 48%) as a yellowish solid: mp 260-262° C. 1H NMR (400 MHz, DMSO-d6) δ 11.79 (s, 1H), 9.76 (s, 1H), 7.84 (d, J=8.4 Hz, 1H), 7.56 (brs, 1H), 7.26 (d, J=8.8 Hz, 1H), 7.23 (brs, 1H), 7.11 (brs, 2H), 2.25 (s, 3H); 13C NMR (100 MHz, DMSO-d6) δ 169.7, 161.9, 152.5, 148.4, 131.9, 125.6, 120.0, 119.6, 119.4, 102.5, 24.6; HRMS (ESI) Calcd for $C_{12}H_{12}N_5O^+$ (M+H)$^+$ 242.10364. Found 242.10359.

Example 32

Synthesis of Compound 7b

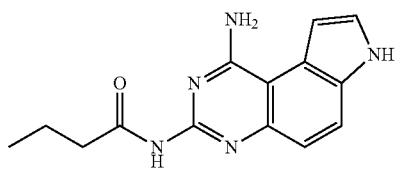

Compound 7b

From 32 mg of 6b, and after column chromatography on silica gel, eluting with 1.5:1 EtOAc:THF containing 1% DIPEA, compound 7b (14 mg, 44% yield) was obtained as a yellowish solid: mp 228-230° C. 1H NMR (400 MHz, DMSO-d6) δ 11.79 (s, 1H), 9.73 (s, 1H), 7.83 (d, J=8.8 Hz, 1H), 7.56 (t, J=2.4 Hz, 1H), 7.27 (d, J=8.8 Hz, 1H), 7.24 (brs, 1H), 7.10 (brs, 2H), 2.56 (q, J=7.6 Hz, 2H), 1.07 (t, J=7.6 Hz, 3H); 13C NMR (100 MHz, DMSO-d6) δ 172.8, 161.9, 152.4, 148.4, 131.9, 125.6, 120.0, 119.6, 119.4, 104.8, 102.5, 29.5, 9.6; HRMS (ESI) Calcd for $C_{13}H_{14}N_5O^+$ (M+H)$^+$ 256.11929. Found 256.11913.

Example 33

Synthesis of Compound 7c

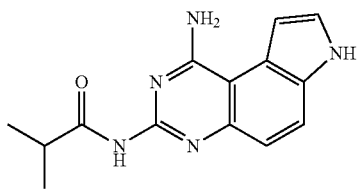

Compound 7c

From 35 mg of 6c, and after column chromatography on silica gel, eluting with 1.5:1 EtOAc:THF containing 1% DIPEA, compound 7c (13 mg, 37% yield) was obtained as a yellowish solid: mp 262-264° C. 1H NMR (400 MHz, DMSO-d6) δ 11.79 (s, 1H), 9.74 (s, 1H), 7.83 (d, J=8.8 Hz, 1H), 7.56 (t, J=2.4 Hz, 1H), 7.27 (d, J=9.2 Hz, 1H), 7.24 (brs, 1H), 7.09 (brs, 2H), two protons were buried in residual DMSO signal, 1.60 (sextet, J=7.2 Hz, 2H), 0.93 (t, J=7.6 Hz, 3H); 13C NMR (100 MHz, DMSO-d6) δ 171.8, 161.9, 152.4, 148.4, 131.9, 125.6, 120.0, 119.6, 119.4, 104.8, 102.5, 38.1, 18.4, 13.8; HRMS (ESI) Calcd for $C_{14}H_{16}N_5O^+$ (M+H)$^+$ 270.13494. Found 270.13474.

Example 34

Synthesis of Compound 7d

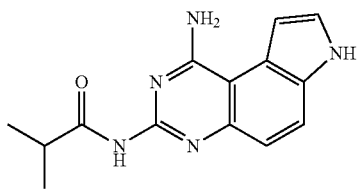

Compound 7d

From 35 mg of 6d, and after column chromatography on silica gel, eluting with 2:1 EtOAc:THF containing 1%

DIPEA, compound 7d (14 mg, 40% yield) was obtained as a yellowish solid: mp 288-290° C. 1H NMR (400 MHz, DMSO-d6) δ 11.79 (s, 1H), 9.79 (s, 1H), 7.83 (d, J=9.2 Hz, 1H), 7.56 (t, J=2.8 Hz, 1H), 7.27 (d, J=9.2 Hz, 1H), 7.24 (brs, 1H), 7.08 (brs, 2H), 2.92 (brs, 1H), 1.08 (d, J=6.8 Hz, 6H); 13C NMR (100 MHz, DMSO-d6) δ 175.3, 162.0, 152.4, 148.4, 131.9, 125.6, 120.0, 119.6, 119.4, 105.0, 102.6, 34.1, 19.5; HRMS (ESI) Calcd for $C_{14}H_{16}N_5O^+$ (M+H)$^+$ 270.13494. Found 270.13484.

Example 35

Synthesis of Compound 7e

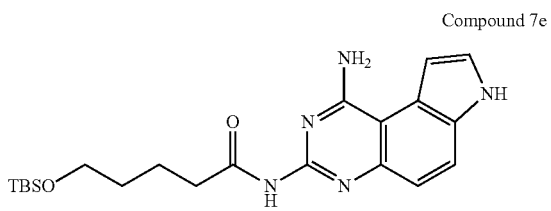 [SMILES: CC(C)(C)[Si](C)(C)OCCCCC(=O)Nc1nc(N)c2c(ccc3[nH]ccc32)n1]

Compound 7e

From 80 mg of 6e, and after column chromatography on silica gel, eluting with 4:1 EtOAc:THF containing 1% DIPEA, compound 7e (40 mg, 50% yield) was obtained as a light green solid after treating with NH$_4$OH (3 mL) and hexanes (3 mL) successively: mp 140-142° C. 1H NMR (400 MHz, DMSO-d6) δ 11.77 (s, 1H), 9.74 (s, 1H), 7.83 (d, J=8.8 Hz, 1H), 7.56 (t, J=2.4 Hz, 1H), 7.26 (d, J=9.2 Hz, 1H), 7.23 (s, 1H), 7.08 (brs, 2H), 3.60 (t, J=6.0 Hz, 2H), two protons were buried in residual DMSO signal, 1.65-1.57 (m, 2H), 1.54-1.47 (m, 2H), 0.85 (s, 9H), 0.02 (s, 6H); 13C NMR (100 MHz, DMSO-d6) δ 172.0, 162.9, 152.4, 148.4, 131.9, 125.6, 120.0, 119.6, 119.4, 104.9, 102.6, 62.4, 35.9, 32.0, 25.9, 21.5, 18.0, −5.2; HRMS (ESI) Calcd for $C_{21}H_{32}N_5O_2Si^+$ (M+H)$^+$ 414.23198. Found 414.23145.

Example 36

Synthesis of Compound 7f

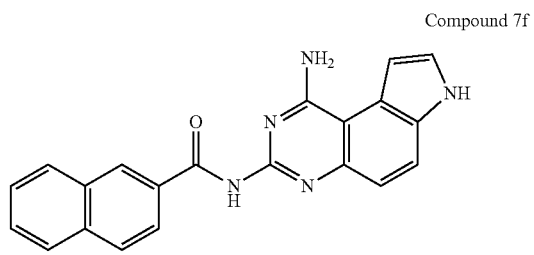 [SMILES: Nc1nc(NC(=O)c2ccc3ccccc3c2)nc2ccc3[nH]ccc3c12]

Compound 7f

From 40 mg of 6f, and after column chromatography on silica gel, eluting with 20:1 EtOAc:THF containing 1% DIPEA, compound 7f (10 mg, 25% yield) was obtained as a yellow solid: mp 234-236° C. 1H NMR (400 MHz, DMSO-d6) δ 11.85 (s, 1H), 10.61 (brs, 1H), 8.65 (s, 1H), 8.08-7.99 (m, 4H), 7.90 (d, J=8.8 Hz, 1H), 7.66-7.60 (m, 3H), 7.39-7.20 (m, 4H); 13C NMR (100 MHz, DMSO-d6) δ 162.3, 152.8, 134.4, 132.4, 132.3, 132.2, 129.2, 128.5, 127.9, 127.8, 127.7, 126.7, 125.9, 124.8, 119.8, 119.4, 105.3, 102.7; HRMS (ESI) Calcd for $C_{21}H_{16}N_5O^+$ (M+H)$^+$ 354.13494. Found 354.13478.

Example 37

Synthesis of N-(1-Amino-7H-pyrrolo[3,2-f]quinazolin-3-yl)-3-butoxy-2-naphthamide 7g

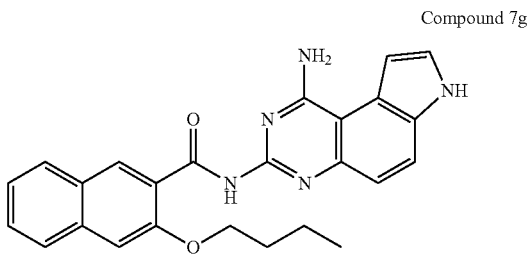 [SMILES: CCCCOc1cc2ccccc2cc1C(=O)Nc1nc(N)c2c(ccc3[nH]ccc32)n1]

Compound 7g

From 120 mg of 6g and after column chromatography on silica gel, eluting with 2:1 DCM:THF, 7g was obtained as a yellow solid (58 mg, 48% yield). mp 205-207° C. $^1$H NMR (400 MHz, DMSO-d$_6$) δ 11.88 (s, 1H), 10.62 (s, 1H), 8.38 (s, 1H), 8.00 (d, J=8.0 Hz, 1H), 7.90-7.87 (m, 2H), 7.63 (t, J=6.4 Hz, 1H), 7.59-7.55 (m, 1H), 7.52 (brs, 1H), 7.44-7.30 (m, 5H), 4.21 (brs, 2H), 1.83 (brs, 2H), 1.53 (brs, 2H), 0.93 (t, J=7.6 Hz, 3H). $^{13}$C NMR (100 MHz, DMSO-d$_6$) δ 164.1, 162.1, 153.7, 151.4, 145.9, 135.4, 132.3, 131.2, 128.6, 128.1, 127.6, 126.5, 126.3, 125.3, 124.4, 120.1, 119.4, 118.7, 107.5, 104.9, 102.5, 68.5, 30.6, 18.9, 13.8.

Example 38

Identification of Nuclear Lamins as Potential Molecular Targets of 7f

Figure 5A:
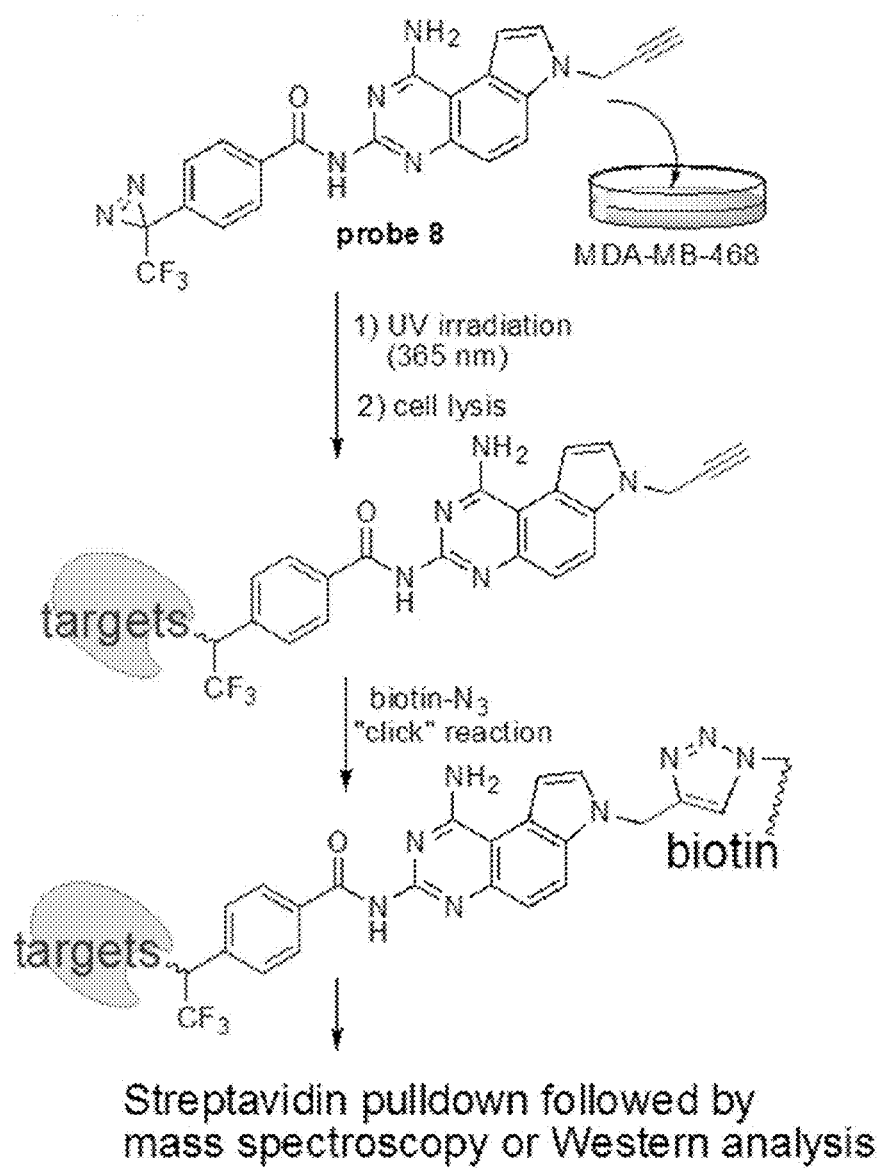
FIG. 5A is a schematic diagram of chemoproteomics experiments described in Example 38 below. MDA-MB-468 cells were treated with probe 10 with or without compound 7f. Then the cells were irradiated by UV followed by cell lysis. The lysates were clicked with a biotin-$N_3$. The biotinylated proteins were pulled down with streptavidin beads. The bound proteins were trypsin-digested for LC-MS/MS analysis or eluted for Western analysis.
Figure 5B:
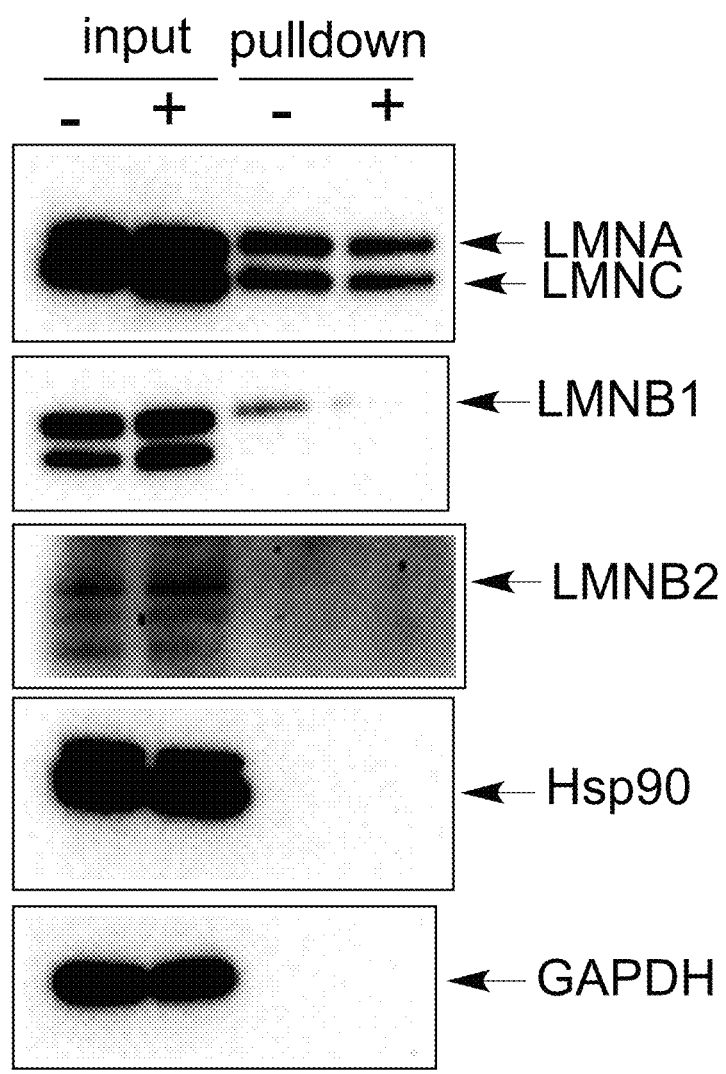
FIG. 5B is an image of a Western blot showing that 7f binds LMNA and LMNB1. The proteins from streptavidin-pulldown prepared as shown in FIG. 5A were subjected to Western blot with antibodies specific for the proteins indicated by the arrows to the right of the figure.

Unbiased chemical proteomics experiments involving photocrosslinking MDA-MB-468 cells treated with probe compound 10, clicking with a biotin-azide (biotin-N$_3$), streptavidin pulldown and mass spectroscopic analyses identified nuclear lamins as the molecular targets of 7f. Nuclear lamins are type V intermediate filament proteins. In humans, there are three lamin genes (LMNA, LMNB1 and LMNB2) encoding four major proteins: LMNA, LMNC, LMNB1 and LMNB2. To further confirm that lamins are the targets, the biotinylated proteins prepared as shown in FIG. 5A were pulled down and analyzed by Western blot with individual antibodies (FIG. 5B). This analysis clearly showed that LMNA/C and LMNB1 were pulled down and competed by 7f.

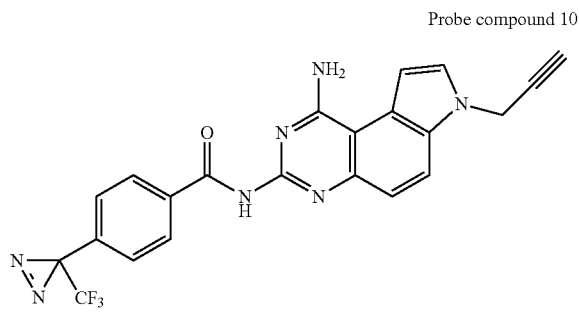 [SMILES: C#CCn1ccc2c3c(N)nc(NC(=O)c4ccc(C5(C(F)(F)F)N=N5)cc4)nc3ccc21]

Probe compound 10

What is claimed is:

1. A compound of formula (I):

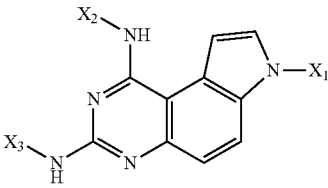

wherein $X_1$ is H and $X_2$, and $X_3$ are independently H or acyl provided that $X_2$, and $X_3$ are not both H.

2. The compound of claim 1 comprising a compound of formula (III)

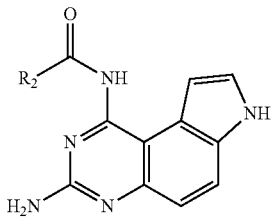

wherein $R_2$ is lower alkyl, ether, or aryl.

3. The compound of claim 2 wherein $R_2$ is methyl, ethyl, propyl, isopropyl, silyl ether, phenyl, substituted phenyl, naphthyl or substituted naphthyl.

4. The compound of claim 1 comprising a compound of formula (IV)

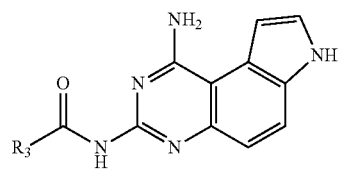

wherein $R_3$ is lower alkyl, ether, or aryl.

5. The compound of claim 4 wherein $R_3$ is methyl, ethyl, propyl, isopropyl, silyl ether, phenyl, substituted phenyl, naphthyl, or substituted naphthyl.

6. The compound of claim 5 wherein $R_3$ is an ether substituted naphthyl.

7. The compound of claim 6 wherein $R_3$ is selected from an unsubstituted naphthyl and a 3-butoxy naphthyl.

8. A pharmaceutical composition comprising a therapeutically effective amount of the compound of claim 1 and a pharmaceutically acceptable salt.

9. The pharmaceutical composition of claim 8 further comprising a pharmaceutically acceptable carrier.

* * * * *